(12) United States Patent
Wei et al.

(10) Patent No.: US 10,722,582 B2
(45) Date of Patent: Jul. 28, 2020

(54) TARGETED ANTIMICROBIAL PHOTODYNAMIC THERAPY

(71) Applicant: Purdue Research Foundation, West Lafayette, IN (US)

(72) Inventors: Alexander Wei, West Lafayette, IN (US); Ana Victoria Morales-de-Echegaray, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/370,153

(22) Filed: Mar. 29, 2019

(65) Prior Publication Data

US 2019/0314502 A1 Oct. 17, 2019

Related U.S. Application Data

(60) Provisional application No. 62/656,620, filed on Apr. 12, 2018.

(51) Int. Cl.
| | | |
|---|---|---|
| *A61K 9/00* | (2006.01) | |
| *A61K 41/00* | (2020.01) | |
| *A61P 31/04* | (2006.01) | |
| *A61K 47/69* | (2017.01) | |
| *A61K 47/64* | (2017.01) | |

(52) U.S. Cl.
CPC ........ *A61K 41/0071* (2013.01); *A61K 9/0014* (2013.01); *A61P 31/04* (2018.01); *A61K 47/64* (2017.08); *A61K 47/6929* (2017.08)

(58) Field of Classification Search
CPC .................................................. A61K 41/0071
See application file for complete search history.

(56) References Cited

U.S. PATENT DOCUMENTS

| 2004/0143001 A1* | 7/2004 | Love | C07D 487/22 514/410 |
|---|---|---|---|
| 2011/0112464 A1* | 5/2011 | Roncucci | C07D 487/22 604/20 |

FOREIGN PATENT DOCUMENTS

WO WO-2006077877 A1 * 7/2006 ........... B29C 55/285

OTHER PUBLICATIONS

Tarai, B., et al, "Recurrent challenges for clinicians: Emergence of methicillin-resistant *Staphylococcus aureus*, vancomycin resistance, and current treatment options", J. Lab. Physicians 5, 71-78. 2013, pp. 10.

(Continued)

*Primary Examiner* — Paul W Dickinson
(74) *Attorney, Agent, or Firm* — Purdue Research Foundation; Liang Zeng Yan

(57) ABSTRACT

The present application relates generally to a method and a composition matter that provides a rapid and potent antimicrobial photodynamic inactivation (aPDI) of pathogenic bacteria that express high-affinity cell-surface hemin receptors (CSHRs) using Ga(III)-protoporphyrins IX (GaPpIX or Ga-PpIX). The invention provides an effective treatment option for infections of skin or body cavities that are accessible to visible-light irradiation, such as a handheld LED array emitting visible light (405 nm), especially for infections caused by *Staphylococcus aureus*, Methicillin-resistant *Staphylococcus aureus* (MRSA), pathogenic staphylococci, *Streptococcus mutans*, *S. pneumoniae*, *S. pyogenes*, streptococci, corynebacteria, mycobacteria, and *Bacillus anthracis*.

10 Claims, 9 Drawing Sheets

(56) References Cited

OTHER PUBLICATIONS

Rutala, W., et al, "Guideline for disinfection and sterilization in healthcare facilities", Center for Disease Control and Prevention, 2008, pp. 161.

Mazurek, J., et al, Work-related asthma in the educational services industry: California, Massachusetts, Michigan, and New Jersey, 1993-2000, Am. J. Ind. Med. 51, 2008, pp. 47-59.

Aiello, A., et al, "Antibacterial cleaning and hygiene products as an emerging risk factor for antibiotic resistance in the community" The Lancet Infect. Dis., 3, 2003, pp. 501-506.

Hamblin P., et al, "Photodynamic therapy: a new antimicrobial approach to infectious disease?", Photochem. Photobiol. Sci. 3, 2004, pp. 436-450.

Giuliana F., et al, "In vitro resistance selection studies of RLP068/CI, a new Zn(II) phthalocyanine suitable for antimicrobial photodynamic therapy", Antimicrob. Agents Chemother. 54, 2010, pp. 637-642.

Pilpa, R., et al, "Functionally distinct NEAT (NEAr Transporter) domains within the *Staphylococcus aureus* IsdH/HarA protein extract heme from methemoglobin", J. Biol. Chem. 284, 2009, pp. 1166-1176.

Hu, Y., et al., "Potential of protoporphyrin IX and metal derivatives for single molecule fluorescence studies", J. Luminescence 131, 2011, pp. 477-481.

Olczak, T., "Gallium(III), cobalt(III) and copper(II) protoporphyrin IX exhibit antimicrobial activity against Porphyromonas gingivalis by reducing planktonic and biofilm growth and invasion of host epithelial cells", Arch. Microbiol., 194, 2012, pp. 719-724.

Nakonieczna, J., "Photoinactivation of *Staphylococcus aureus* using protoporphyrin IX: the role of haem-regulated transporter HrtA", Appl. Microbiol. Biotechnol. 100, 2016, pp. 1393-1405.

Maltais, T., et al., "Label-free detection and discrimination of bacterial pathogens based on hemin recognition", Bioconjugate Chem. 27, 2016, pp. 1713-1722.

Hammer, N., et al, "Molecular mechanisms of *Staphylococcus aureus* iron acquisition", Annu. Rev. Microbiol. 65, 2011, pp. 129-147.

Maresso, A.,et al, "Bacillus anthracis secretes proteins that mediate heme acquisition from hemoglobin", PLoS. Pathog. 4, 2008, pp. 12.

Eichner, A., et al, "Dirty hands: photodynamic killing of human pathogens like EHEC, MRSA and Candida seconds", Photochem. Photobiol. Sci. 12, 2013, pp. 135-147.

Eckl, D., et al, "A Closer Look at Dark Toxicity of the Photosensitizer TMPyP in Bacteria", Photochem. Photobiol., in press., 2018, pp. 165-172.

Nakonieczna, J., et al, "Photodynamic inactivation requires innovative approach concerning numerous bacterial isolates and multicomponent sensitizing agents", Photodiagn. Photodyn. Ther. 9, 2012, pp. 359-361.

Gonzalez-Delgado, J., et al, "Use of photosensitizers in semisolid formulations for microbial photodynamic inactivation", J. Med. Chem. 59, 2015, pp. 4428-4442.

Moriwaki, Y., et al, Molecular basis of recognition of antibacterial porphyrins by heme-transporter IsdH-NEAT3 of *Staphylococcus aureus*. Biochemistry 50, 2011, pp. 7311-7230.

Bohle, D., et al, Soluble diamagnetic model for malaria pigment: Coordination chemistry of gallium(III) protoporphyrin-IX. Inorg. Chem. 51, 2012, pp. 10747-10761.

Clark, E., et al, "Photosensitized H2 production using a zinc porphyrin-substituted protein, platinum nanoparticles, and ascorbate with no electron relay: participation of Good's buffers", Inorg. Chem. 56, 2017, pp. 4584-4593.

Lacey J. "The photosensitisation of *Escherichia coil* using disulphonated aluminium phthalocyanine", Journal of Photochemistry and Photobiology, 142, 2001, pp. 145-150.

\* cited by examiner

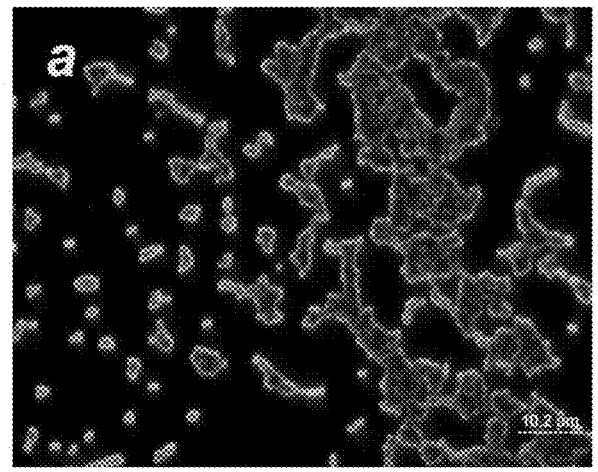
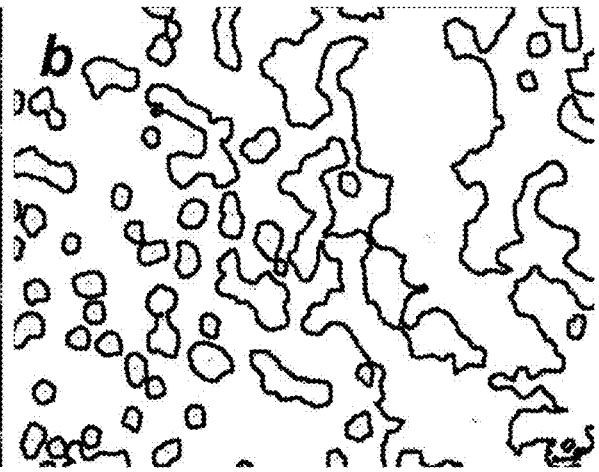
FIG. 8A    FIG. 8B
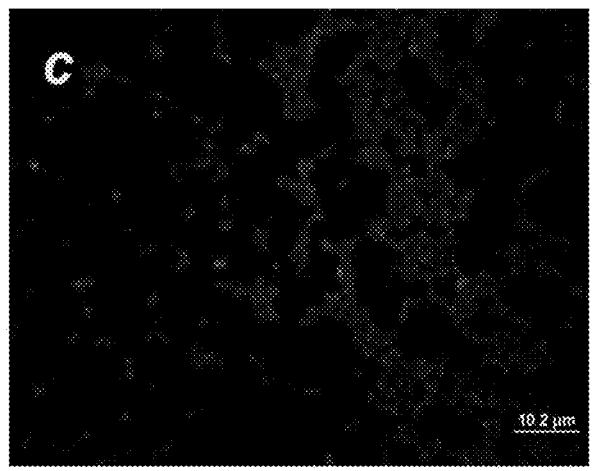
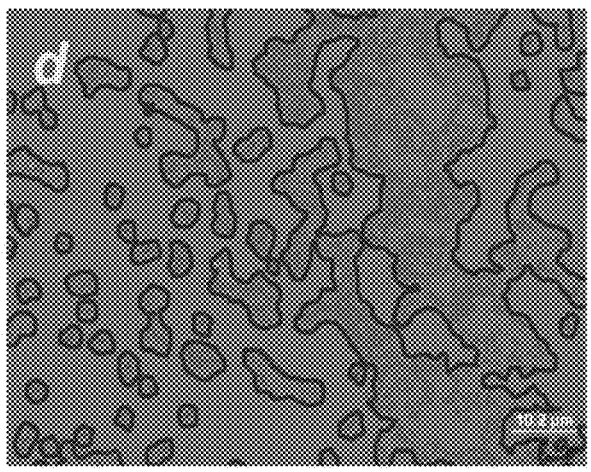
FIG. 8C    FIG. 8D

TARGETED ANTIMICROBIAL PHOTODYNAMIC THERAPY

CROSS REFERENCE TO RELATED APPLICATIONS

This present patent application relates to and claims the priority benefit of U.S. Provisional Application Ser. No. 62/656,620, filed Apr. 12, 2018, the content of which is hereby incorporated herein by reference in its entirety.

TECHNICAL FIELD

The present application relates generally to a method and a composition matter that provides a rapid and potent antimicrobial photodynamic inactivation (aPDI) of pathogenic bacteria that express high-affinity cell-surface hemin receptors (CSHRs) using Ga(III)-protoporphyrins IX (GaPpIX or Ga-PpIX). The invention provides an effective treatment option for infections of skin or body cavities that are accessible to visible-light irradiation, such as a handheld LED array emitting visible light (405 nm), especially infections by those drug-resistant strains.

BACKGROUND

This section introduces aspects that may help facilitate a better understanding of the disclosure. Accordingly, these statements are to be read in this light and are not to be understood as admissions about what is or is not prior art.

Pathogenic Gram-positive bacteria and mycobacteria are remarkably resilient to physical and environ-mental stress, and present serious threats to biosecurity and public health (Cotter, P D, et al., *Mol. Biol. Rev.* 2003, 67, 429-453). Major pathogens include *Staphylococcus aureus*, a leading cause of hospital-acquired infections with multidrug-resistant strains now widely prevalent; *Bacillus anthracis*, which can be weaponized as a biological warfare agent with 50-90% mortality rate upon inhalation or ingestion; and *Streptococcus pneumoniae*, an agent of community-acquired pneumonia especially among young children (Tarai, B. et al., *J. Lab. Physicians* 2013, 5, 71-78; Spencer, R C, *J. Clin. Pathol.* 2003, 56, 182-187; World Health Organization (2014). *Antimicrobial resistance: Global Report on Surveillance.* Fact Sheet No. 194). These pathogens are readily transmitted by physical contact, creating enormous concerns for adequate disinfection in hospitals and public facilities. The problem is compounded by the hazards posed to human health by harsh disinfectants, and by the rise of multidrug-resistant strains (Aiello, A E, et al., *Lancet Infect. Dis.* 2003, 3, 501-506). There are unmet needs in fighting infections by various microorganisms.

SUMMARY OF THE INVENTION

This present invention generally relates generally to rapid and potent antimicrobial photodynamic inactivation (aPDI) of pathogenic bacteria that express high-affinity cell-surface hemin receptors (CSHRs) using an analog of hemin, such as GaPpIX. Bacteria of particular interest for the present invention include staphylococci, streptococci, mycobacteria, *Bacillus anthracis*, and others. The invention is intended for the treatment of skin infections or body cavities that are accessible to visible-light irradiation. Pharmaceutical compositions and methods of use are within the scope of this invention.

In some illustrative embodiments, the present invention relates to a method for treating an infection caused by a bacteria comprising the steps of
a. applying a therapeutically effective amount of a metal-complexed porphyrin photosensitizer to an infected area; and then
b. exposing said infected area to a light for a period of time.

In some illustrative embodiments, the present invention relates to a method for treating an infection caused by a bacteria disclosed herein further comprising a step of adding a targeting protein or a nanoparticle to said photo sensitizer.

In some illustrative embodiments, the present invention relates to a method for treating an infection caused by a bacteria disclosed herein further comprising a step of conjugating said photosensitizer to a targeting protein or a nanoparticle.

In some illustrative embodiments, the present invention relates to a method for treating an infection caused by a bacteria disclosed herein, wherein said nanoparticle is a silver or gold nanoparticle.

In some illustrative embodiments, the present invention relates to a method for treating an infection caused by a bacteria disclosed herein further comprising a step of conjugating said photosensitizer to a targeting protein or a nanoparticle.

In some illustrative embodiments, the present invention relates to a method for treating an infection caused by a bacteria disclosed herein further comprising a step of adding an aminoglycoside antibiotic to said photo sensitizer.

In some illustrative embodiments, the present invention relates to a method for treating an infection caused by a bacteria disclosed herein, wherein said metal-complexed porphyrin has a formula (I)

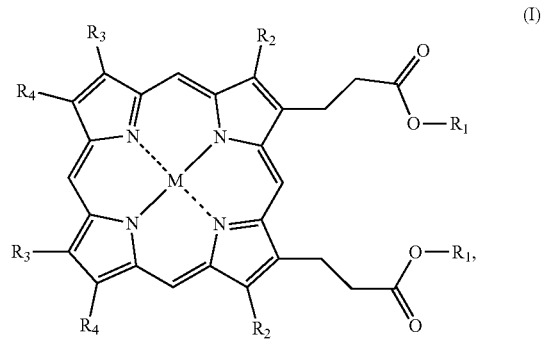

or a pharmaceutically acceptable salt thereof, wherein
M is a metal or coordinated metal ion;
$R_1$ is hydrogen, an alkyl, or a substituted alkyl;
$R_2$ is an alkyl, or a substituted alkyl;
$R_3$ is an acyl, alkenyl, α-hydroxyalkyl, aryl, or aromatic heterocycle, each of
which is optionally substituted; and
$R_4$ is an alkyl, or a substituted alkyl.

In some illustrative embodiments, the present invention relates to a method for treating an infection caused by a bacteria disclosed herein, wherein said metal-complexed porphyrin has a formula (I), wherein $R_2$ and $R_4$ are methyl; $R_3$ is vinyl; and $R_1$ is methyl or hydrogen.

In some illustrative embodiments, the present invention relates to a method for treating an infection caused by a bacteria disclosed herein, wherein said metal-complexed porphyrin has a formula (I) wherein M is a halo coordinated ion of magnesium, iron, manganese, cobalt, nickel, copper, zinc, and gallium.

In some illustrative embodiments, the present invention relates to a method for treating an infection caused by a bacteria disclosed herein, wherein said metal-complexed porphyrin has a formula (I) wherein M is Ga(III)Cl.

In some illustrative embodiments, the present invention relates to a method for treating an infection caused by a bacteria disclosed herein, wherein said light is a visible or infrared light.

In some illustrative embodiments, the present invention relates to a method for treating an infection caused by a bacteria disclosed herein, wherein said light is a visible light of $\lambda_{max}$ about 405 nm.

In some illustrative embodiments, the present invention relates to a method for treating an infection caused by a bacteria disclosed herein, wherein said infected area is a topical skin, a body or an inner body cavity that is accessible to light irradiation.

In some illustrative embodiments, the present invention relates to a method for treating an infection caused by a bacteria disclosed herein, wherein said bacteria express a high-affinity cell-surface hemin receptor.

In some illustrative embodiments, the present invention relates to a method for treating an infection caused by a bacteria disclosed herein, wherein said bacteria comprises *Staphylococcus aureus*, Methicillin-resistant *Staphylococcus aureus* (MRSA), vancomycin resistant *S. aureus* (VRSA), *S. epidermidis*, pathogenic staphylococci, *Streptococcus mutans*, *S. pneumoniae*, *S. pyogenes*, streptococci, corynebacteria, mycobacteria, and *Bacillus anthracis*.

In some illustrative embodiments, the present invention relates to a method for treating an infection caused by a bacteria disclosed herein, wherein said staphylococci comprises *Staphylococcus aureus* and its drug-resistant variants methicillin-resistant *S. aureus* (MRSA) and vancomycin resistant *S. aureus* (VRSA), *S. epidermidis*, and said streptococci comprises *Streptococcus mutans*, *S. pneumoniae*, *S. pyogenes*, and group B streptococci.

In some other illustrative embodiments, the present invention relates to a pharmaceutical composition for the treatment of topical infection caused by a bacterium expressing a high-affinity cell-surface hemin receptor comprising a photo sensitizer of formula (I)

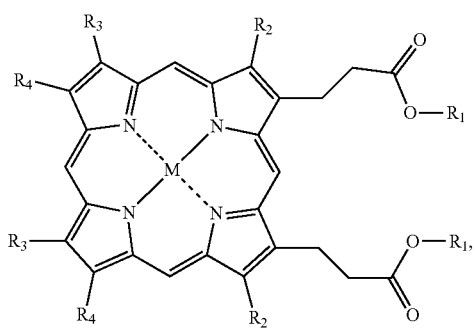

(I)

or a pharmaceutically acceptable salt thereof, together with one or more pharmaceutically acceptable diluents, excipients or carriers, wherein
  M is a metal or coordinated metal ion;
  $R_1$ is hydrogen, an alkyl, or a substituted alkyl;
  $R_2$ is an alkyl, or a substituted alkyl;
  $R_3$ is an acyl, alkenyl, α-hydroxyalkyl, aryl, or aromatic heterocycle, each of which is optionally substituted;
  and $R_4$ is an alkyl, or a substituted alkyl.

In some other illustrative embodiments, the present invention relates to a pharmaceutical composition for the treatment of an infection caused by a bacterium disclosed herein, wherein said pharmaceutical composition is a cream formulation for topical application.

In some other illustrative embodiments, the present invention relates to a pharmaceutical composition for the treatment of an infection caused by a bacterium disclosed herein, wherein said pharmaceutical composition further comprises a targeting protein or a nanoparticle.

In some other illustrative embodiments, the present invention relates to a pharmaceutical composition for the treatment of an infection caused by a bacterium disclosed herein, wherein said pharmaceutical composition as disclosed herein, wherein said nanoparticle is a silver or gold nanoparticle.

In some other illustrative embodiments, the present invention relates to a pharmaceutical composition for the treatment of an infection caused by a bacterium disclosed herein, wherein said pharmaceutical composition further comprises an aminoglycoside antibiotic.

In some other illustrative embodiments, the present invention relates to a pharmaceutical composition for the treatment of topical infection caused by a bacterium expressing a high-affinity cell-surface hemin receptor comprising a compound of formula (I), wherein $R_2$ and $R_4$ are methyl; $R_3$ is vinyl; and $R_1$ is methyl or hydrogen.

In some other illustrative embodiments, the present invention relates to a pharmaceutical composition for the treatment of topical infection caused by a bacterium expressing a high-affinity cell-surface hemin receptor comprising a compound of formula (I), wherein M is a halo coordinated ion of magnesium, iron, manganese, cobalt, nickel, copper, zinc, and gallium.

In some other illustrative embodiments, the present invention relates to a pharmaceutical composition for the treatment of topical infection caused by a bacterium expressing a high-affinity cell-surface hemin receptor comprising a photo sensitizer of formula (II)

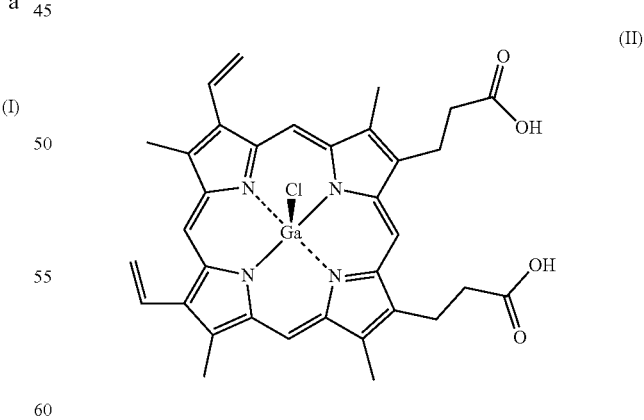

(II)

or a pharmaceutically acceptable salt thereof, together with one or more pharmaceutically acceptable diluents, excipients or carriers.

These and other features, aspects and advantages of the present invention will become better understood with reference to the following drawings, detailed description and claims.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIG. 3A *S. aureus* after 15 min incubation; FIGS. 3B-3D show *Y. enterocolitica* (a hemophore-expressing pathogen) after 15, 30, and 60 min incubation.

FIGS. 8A-8D show fluorescence image analysis. In this example, a suspension of *S. aureus* (10$^8$ cfu/mL) was treated with Ga-PpIX (7.3 µM) for 15 min, then washed three times with water before being deposited onto glass coverslips. FIGS. 8A-8B show darkfield images were acquired and processed to obtain ROIs containing bacteria; FIGS. 8C-8D show fluorescence images ($\lambda_{em}$>570 nm) were acquired and superimposed with the bacteria map defined above. Fluorescence intensities from Ga-PpIX staining are based on the mean pixel value within all ROIs.

DETAILED DESCRIPTION

Figure 1:
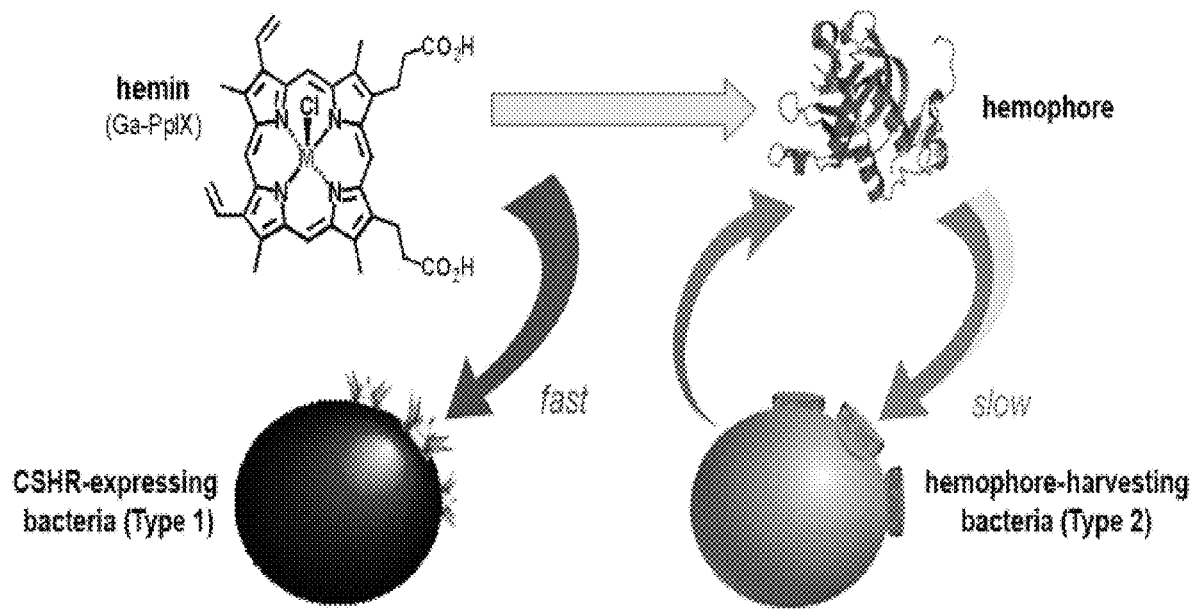
FIG. 1 shows CSHR-expressing bacteria (Type 1) and hemophore-harvesting strains (Type 2), distinguished by their rates of hemin (or Ga-PpIX) uptake (Maltais, T. R. et al, *Bioconjugate Chem.* 2016, 27, 1713-1722; Morales-de-Echegaray, A. V. et al, *ACS Infect. Dis.* 2018, 4, 1564-1573).

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 20%, within 10%, within 5%, or within 1% of a stated value or of a stated limit of a range.

In the present disclosure the term "substantially" can allow for a degree of variability in a value or range, for example, within 80%, within 90%, within 95%, or within 99% of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH=CH—, —CH=CHCH$_2$—, and the like. Examples of branched alkenyl groups include, but are not limited to, —CH=C (CH$_3$)— and the like.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups.

Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 μg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

This invention concerns rapid and potent antimicrobial photodynamic inactivation (aPDI) of pathogenic bacteria that express high-affinity cell-surface hemin receptors (CSHRs) using GaPpIX, a photoactive analog of hemin. Bacteria of particular interest include *Staphylococcus aureus* and its drug-resistant variants (MRSA and VRSA), streptococci including *Streptococcus mutans, S. pneumoniae, S. pyogenes*, and group B streptococci, cornyebacteria, mycobacteria, and *Bacillus anthracis*. The invention is intended to support topical applications of aPDI, for skin infections or body cavities that are accessible to visible-light irradiation.

GaPpIX has been previously reported to have antibiotic activity against multiple strains of bacteria, and low collateral (dark) toxicity against mammalian cells. However, the photophysical properties of GaPpIX, including fluorescence and singlet-oxygen quantum yields, were essentially unknown prior to our studies, except Bhaumik, J. (2007) Synthetic Porphyrinic Macrocycles for Photodynamic Therapy and Other Biological Applications, Ph.D. Thesis, North Carolina State University, Raleigh, N.C.

Bacteria that express CSHRs are highly susceptible to rapid aPDI using hemin analogs, particularly GaPpIX. Bacteria that rely on hemophores for hemin acquisition may also be susceptible to aPDI by GaPpIX, but their uptake rates are slower (30 minutes or longer) which has an indirect effect on potency.

Other porphyrin-based photosensitizers (PpIX, chlorin-e6, HpD/Photofrin, PTMPP, TMPyP) have been used for aPDI against *S. aureus* and MRSA, but their entry into bacteria does not depend on hemin-specific acquisition pathways such as CSHR uptake. Many of these photosensitizers are rendered cytotoxic for lack of a pathogen-specific targeting and uptake mechanism. For example, TMPyP is cytotoxic against HEK cells, with an $IC_{50}$ between 0.5 and 1.0 μM. In comparison, the $IC_{50}$ of GaPpIX is well above 10 μM.

In some illustrative embodiments, GaPpIX and other metallated PpIX species were discovered as a remarkably potent photo sensitizer that is activated at visible wavelengths (about 405 nm).

In some illustrative embodiments, GaPpIX and other metallated PpIX species were taken up by CSHR-expressing bacteria within seconds of exposure, with saturation achieved in under 15 minutes. Moreover, GaPpIX uptake is specifically mediated by CSHRs, as determined by a competitive uptake study with hemin.

In some illustrative embodiments, GaPpIX and other metallated PpIX species were able to achieve 3-log reduction by aPDI against *S. aureus* and clinical isolates of MRSA can be achieved at low micromolar concentrations of GaPpIX (0.5-4.5 μM) using 15 minutes of irradiation from a compact fluorescence lightbulb ($\lambda_{max}$ 406 nm, 12.4 mW/cm$^2$).

In some illustrative embodiments, GaPpIX and other metallated PpIX species functioned as aPDI showed efficacy at nanomolar concentrations of GaPpIX (0.06-0.12 μM) under irradiation of 10 seconds from a 405-nm light-emitting diode bar (99 mW/cm$^2$), at a fluence of about 1 J/cm$^2$.

In some illustrative embodiments, GaPpIX and other metallated PpIX species may be conjugated to proteins and nanoparticles to enable their targeted bacterial uptake with synergistic antimicrobial activity. For example, GaPpIX added to apohemoglobin (Ga-hemoglobin) can be adsorbed onto 10-nm Ag nanoparticles (AgNP), then introduced to *S. aureus* and exposed to 405-nm light irradiation. The photosensitizing activity of GaPpIX is amplified severalfold by the plasmon resonance of the Ag nanoparticle, with a commensurate increase in aPDI potency (GaPpIX effective concentration=0.022-0.080 µM, at a fluence of about 1 J/cm$^2$).

In some illustrative embodiments, GaPpIX and other metallated PpIX species may be conjugated to other antibiotics to enable their targeted bacterial uptake with complementary antimicrobial activity. For example, GaPpIX can be conjugated to amikacin, a ribosomal inhibitor of protein synthesis, with an oxidation-sensitive linker. Amikacin is released by cleaving the linker with singlet oxygen following uptake of the GaPpIX-amikacin conjugate, preventing the bacteria from mounting a survival response to oxidative stress.

In some other illustrative embodiments, the present invention relates to a method for treating an infection caused by a bacteria comprising the steps of
    a. applying a therapeutically effective amount of a metal-complexed porphyrin photosensitizer to an infected area; and then
    b. exposing said infected area to a light for a period of time.

In some other illustrative embodiments, the present invention relates to a method for treating an infection caused by a bacteria disclosed herein further comprising a step of adding a targeting protein or a nanoparticle to said photosensitizer.

In some other illustrative embodiments, the present invention relates to a method for treating an infection caused by a bacteria disclosed herein further comprising a step of conjugating said photosensitizer to a targeting protein or a nanoparticle.

In some other illustrative embodiments, the present invention relates to a method for treating an infection caused by a bacteria disclosed herein, wherein said nanoparticle is a silver or gold nanoparticle.

In some other illustrative embodiments, the present invention relates to a method for treating an infection caused by a bacteria disclosed herein further comprising a step of conjugating said photosensitizer to a targeting protein or a nanoparticle.

In some other illustrative embodiments, the present invention relates to a method for treating an infection caused by a bacteria disclosed herein further comprising a step of adding an aminoglycoside antibiotic to said photo sensitizer.

In some other illustrative embodiments, the present invention relates to a method for treating an infection caused by a bacteria disclosed herein, wherein said metal-complexed porphyrin has a formula (I)

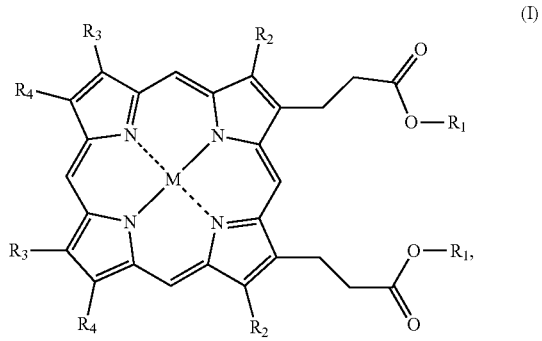

(I)

or a pharmaceutically acceptable salt thereof, wherein
M is a metal or coordinated metal ion;
R$_1$ is hydrogen, an alkyl, or a substituted alkyl;
R$_2$ is an alkyl, or a substituted alkyl;
R$_3$ is an acyl, alkenyl, α-hydroxyalkyl, aryl, or aromatic heterocycle, each of which is optionally substituted; and
R$_4$ is an alkyl, or a substituted alkyl.

In some other illustrative embodiments, the present invention relates to a method for treating an infection caused by a bacteria disclosed herein, wherein said metal-complexed porphyrin has a formula (I), wherein R$_2$ and R$_4$ are methyl; R$_3$ is vinyl; and R$_1$ is methyl or hydrogen.

In some other illustrative embodiments, the present invention relates to a method for treating an infection caused by a bacteria disclosed herein, wherein said metal-complexed porphyrin has a formula (I) wherein M is a halo coordinated ion of magnesium, iron, manganese, cobalt, nickel, copper, zinc, and gallium.

In some other illustrative embodiments, the present invention relates to a method for treating an infection caused by a bacteria disclosed herein, wherein said metal-complexed porphyrin has a formula (I) wherein M is Ga(III)Cl.

In some other illustrative embodiments, the present invention relates to a method for treating an infection caused by a bacteria disclosed herein, wherein said light is a visible or infrared light.

In some other illustrative embodiments, the present invention relates to a method for treating an infection caused by a bacteria disclosed herein, wherein said light is a visible light of λ$_{max}$ about 405 nm.

In some other illustrative embodiments, the present invention relates to a method for treating an infection caused by a bacteria disclosed herein, wherein said infected area is a topical skin, a body or an inner body cavity that is accessible to light irradiation.

In some other illustrative embodiments, the present invention relates to a method for treating an infection caused by a bacteria disclosed herein, wherein said bacteria express a high-affinity cell-surface hemin receptor.

In some other illustrative embodiments, the present invention relates to a method for treating an infection caused by a bacteria disclosed herein, wherein said bacteria comprises *Staphylococcus aureus*, Methicillin-resistant *Staphylococcus aureus* (MRSA), vancomycin resistant *S. aureus* (VRSA), *S. epidermidis*, pathogenic staphylococci, *Streptococcus mutans*, *S. pneumoniae*, *S. pyogenes*, streptococci, corynebacteria, mycobacteria, and *Bacillus anthracis*.

In some other illustrative embodiments, the present invention relates to a method for treating an infection caused by a bacteria disclosed herein, wherein said staphylococci comprises *Staphylococcus aureus* and its drug-resistant variants methicillin-resistant *S. aureus* (MRSA) and vancomycin resistant *S. aureus* (VRSA), *S. epidermidis*, and said streptococci comprises *Streptococcus mutans*, *S. pneumoniae*, *S. pyogenes*, and group B streptococci.

In some other illustrative embodiments, the present invention relates to a pharmaceutical composition for the treatment of topical infection caused by a bacterium expressing a high-affinity cell-surface hemin receptor comprising a photo sensitizer of formula (I)

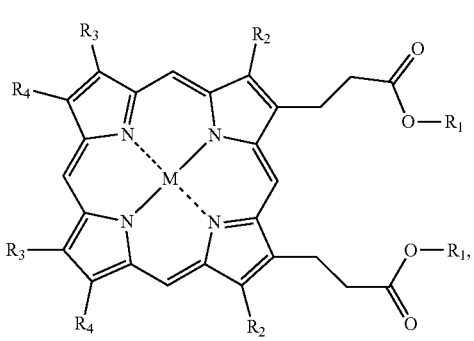 (I)

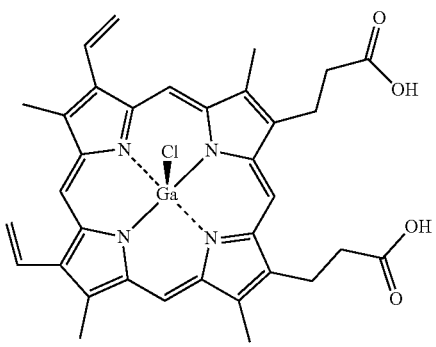 (II)

or a pharmaceutically acceptable salt thereof, together with one or more pharmaceutically acceptable diluents, excipients or carriers, wherein M is a metal or coordinated metal ion;

$R_1$ is hydrogen, an alkyl, or a substituted alkyl;

$R_2$ is an alkyl, or a substituted alkyl;

$R_3$ is an acyl, alkenyl, α-hydroxyalkyl, aryl, or aromatic heterocycle, each of which is optionally substituted; and $R_4$ is an alkyl, or a substituted alkyl.

In some other illustrative embodiments, the present invention relates to a pharmaceutical composition for the treatment of an infection caused by a bacterium disclosed herein, wherein said pharmaceutical composition is a cream formulation for topical application.

In some other illustrative embodiments, the present invention relates to a pharmaceutical composition for the treatment of an infection caused by a bacterium disclosed herein, wherein said pharmaceutical composition further comprises a targeting protein or a nanoparticle.

In some other illustrative embodiments, the present invention relates to a pharmaceutical composition for the treatment of an infection caused by a bacterium disclosed herein, wherein said pharmaceutical composition as disclosed herein, wherein said nanoparticle is a silver or gold nanoparticle.

In some other illustrative embodiments, the present invention relates to a pharmaceutical composition for the treatment of an infection caused by a bacterium disclosed herein, wherein said pharmaceutical composition further comprises an aminoglycoside antibiotic.

In some other illustrative embodiments, the present invention relates to a pharmaceutical composition for the treatment of topical infection caused by a bacterium expressing a high-affinity cell-surface hemin receptor comprising a compound of formula (I), wherein $R_2$ and $R_4$ are methyl; $R_3$ is vinyl; and $R_1$ is methyl or hydrogen.

In some other illustrative embodiments, the present invention relates to a pharmaceutical composition for the treatment of topical infection caused by a bacterium expressing a high-affinity cell-surface hemin receptor comprising a compound of formula (I), wherein M is a halo coordinated ion of magnesium, iron, manganese, cobalt, nickel, copper, zinc, and gallium.

In some other illustrative embodiments, the present invention relates to a pharmaceutical composition for the treatment of topical infection caused by a bacterium expressing a high-affinity cell-surface hemin receptor comprising a photo sensitizer of formula (II)

or a pharmaceutically acceptable salt thereof, together with one or more pharmaceutically acceptable diluents, excipients or carriers.

To fight infections by various microorganisms, one promising countermeasure against drug-resistant pathogens is antimicrobial photodynamic inactivation (aPDI), based on the localized generation of reactive oxygen species by photosensitizers (Hamblin, M R, et al., *Photochem. Photbiol. Sci.* 2004, 3, 436-450). aPDI cannot be easily overcome by known mechanisms of antibiotic resistance, and has been shown to be particularly effective against Gram-positive drug-resistant bacteria such MRSA (Giuliani, F. et al., *Antimicrob. Agents Chemother.* 2010, 54, 637-642; Agrawal, T. et al., *Curr. Pharm. Des.* 2015, 21, 2109-2121). However, many aPDI agents (especially cationic species) are also readily taken up by mammalian cells, compromising their specificity as antimicrobial agents. It is thus important to establish specific mechanisms for the targeted delivery of photo sensitizers.

Bactericidal agents can be delivered to specific pathogens by exploiting molecular uptake pathways associated with virulence or survival. With respect to aPDI, hemin acquisition systems may be considered as natural portals for the uptake of photosensitizers into bacteria. While hemin itself (also known as Fe(III)-protoporphyrin IX, or Fe-PpIX) does not have photosensitizing properties, PpIX and hematoporphyrin (HP) are highly photoactive and are widely used in aPDI (Malik, Z., et al., *J. Photochem. Photobiol. B* 1990, 5, 281-293). Non-iron metalloporphyrins are also excellent candidates for aPDI, as many of these are strongly luminescent and chemically more robust than unmetallated porphyrins (Pilpa, R M, et al., *J. Biol. Chem.* 2009, 284, 1166-1176; Hu, Y. et al., *J. Luminescence* 2011, 131, 477-481; Azad, B B, et al., *Appl. Radiat. Isotop.* 2012, 70, 505-511). Seminal work by Stojiljkovic has shown that non-iron PpIX species are readily taken up by hemin uptake pathways, and also exhibit low collateral toxicity in human cell lines and in rodent models (Stojiljkovic, I. et al., *Mol. Microbiol.* 1999, 31, 429-442). Remarkably, while non-iron PpIX species have been actively investigated as antimicrobial agents (Olczak, T. et al., *Arch. Microbiol.* 2012, 194, 719-724), their utility for aPDI has been mostly overlooked despite the long history of porphyrin-based photosensitizers in photodynamic therapies.

In the broader context of delivering photosensitizers to bacteria, the roles and significance of hemin uptake pathways remain ambiguous, with several unanswered questions regarding specificity and speed of uptake by various pathogens. Indeed, studies aimed at elucidating the roles of specific heme transporters in aPDI are just now emerging (Nakonieczna J. et al., *Appl. Microbiol. Biotechnol.* 2015, 100, 1393-1405). One reason is that bacteria are divergent with respect to hemin harvesting mechanisms: Some are known to express cell-surface hemin receptors (CSHRs) that support a direct acquisition pathway (Type 1), while others rely on the secretion and recovery of extracellular proteins known as hemophores, which introduces an extra step and a subsequent delay in the hemin acquisition process (Type 2; FIG. 1).

In a previous study involving bacterial adhesion using hemin conjugates, we observed certain Gram-positive bacteria such as *Staphylococcus aureus* and *Bacillus anthracis* to bind more quickly (15 minutes or less) than other bacterial species (30 minutes or more), and attributed this to mechanistic differences in hemin acquisition (Maltais, T. R. et al, *Bioconjugate Chem.* 2016, 27, 1713-1722). *S. aureus* and *B. anthracis* both express CSHRs, namely the iron-regulated surface determinant (Isd) family of receptor proteins, enabling them to capture hemin directly and rapidly. This temporal distinction in hemin recognition suggests a specific mechanism for expediting the uptake of hemin-like photosensitizers toward *S. aureus* and other Type 1 bacteria.

Here we focus on Ga(III)-protoporphyrin (Ga-PpIX), a fluorescent analog of hemin, and demonstrate its rapid uptake and potent aPDI against CSHR-expressing pathogens such as *S. aureus*. Ga-PpIX can be taken up by staphylococci within minutes of exposure via CSHR-specific pathways, and exerts antimicrobial activity at nanomolar concentrations when irradiated with a compact fluorescence lightbulb (CFL) operating at visible wavelengths. Ga-PpIX's efficacy as an aPDI agent is consistent against multiple clinical isolates of methicillin-resistant *S. aureus* (MRSA) and *S. epidermidis*. Competitive uptake of hemin against Ga-PpIX, PpIX, and eleven other derivatives establishes the importance of ionic character in uptake specificity. We also observe rapid Ga-PpIX uptake by several other pathogens that use CSHRs for hemin acquisition, broadening the scope of the direct hemin uptake mechanism for pathogen-specific aPDI.

Figure 2:
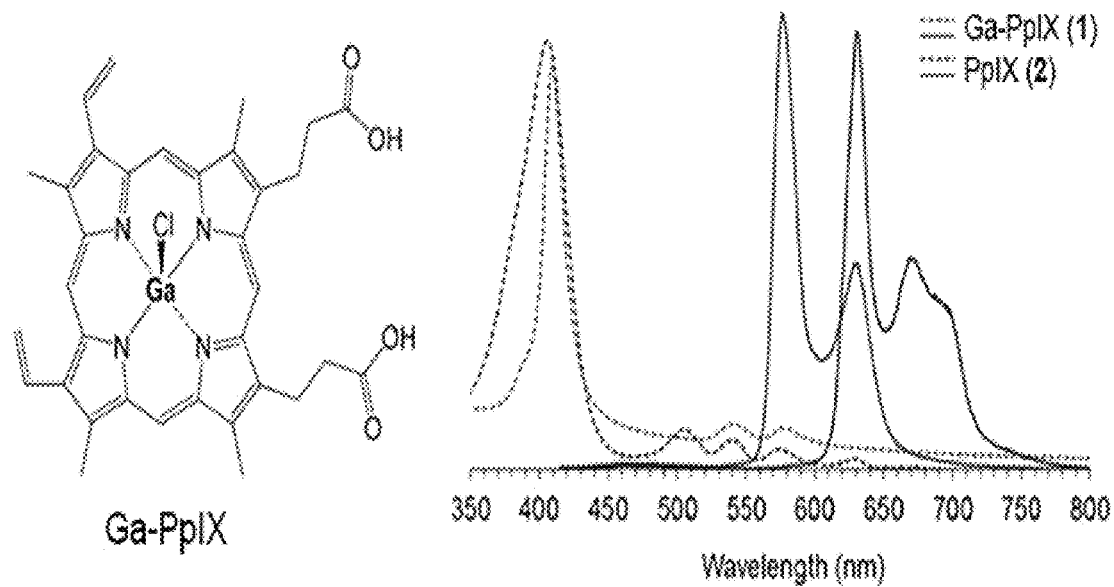
FIG. 2 depicts absorbance (---) and emission (-) spectra for Ga-PpIX (8 µM in DMSO, red) with comparison to PpIX (blue). Structure of Ga-PpIX shown at left.

The luminescent properties of Ga-PpIX have not been previously reported and are briefly described here. Photospectroscopic analysis of Ga-PpIX and PpIX reveals that introducing Ga(III) into the protoporphyrin ring causes the Q bands (475-650 nm) to undergo distinct changes characteristic of metal substitution, but has only a modest effect on the Soret band near 400 nm (FIG. 2). The emission band of Ga-PpIX exhibits a blueshift of over 80 nm, with a primary emission peak at 575 nm and a secondary emission at 628 nm. Ga-PpIX can thus support fluorescence imaging upon UV excitation or at 405 nm (quantum yield $\phi$ 6.3%), and its photostability is sufficient for quantitative image analysis of bacterial labelling and uptake.

To demonstrate that the rapid uptake of Ga-PpIX correlates with CSHR expression and not hemin uptake in general, we compared two bacterial species with well-characterized hemin acquisition systems: *Staphylococcus aureus*, a Gram-positive species that harvests hemoproteins via Isd proteins presented on their cell walls, and *Yersinia enterocolitica*, a Gram-negative species that acquires hemin through HemR, a TonB-dependent hemophore receptor (Stojiljkovic, I. et al, *EMBO J.* 1992, 11, 4359-4367). We hypothesized that (i) one or more Isd proteins on *S. aureus* would be capable of direct hemin capture, and (ii) HemR on *Y. enterocolitica* would be incapable of direct uptake, and delayed by the extra step of hemophore retrieval (FIG. 1).

Figure 3A:
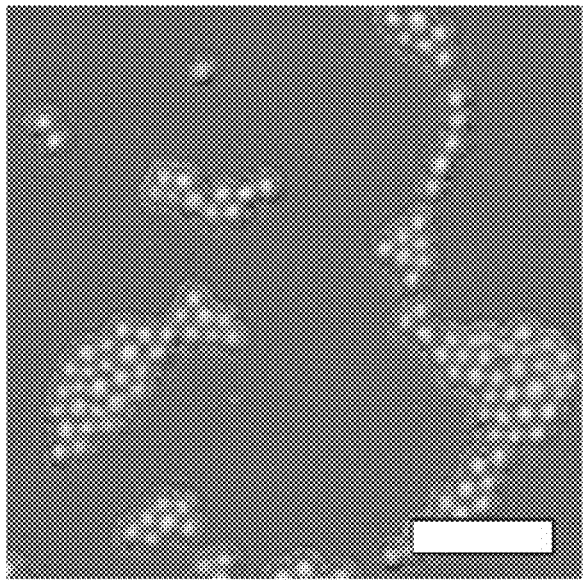
FIGS. 3A-3D demonstrate confocal fluorescence microscopy imaging of Ga-PpIX uptake (bar=5 µm).
Figure 3B:
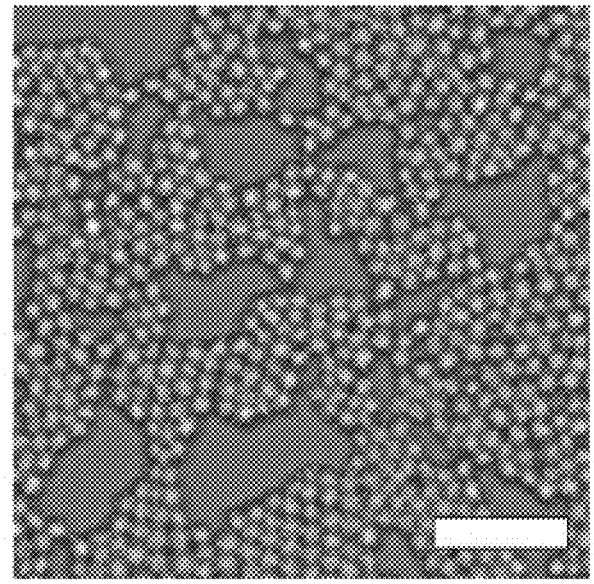
Figure 3C:
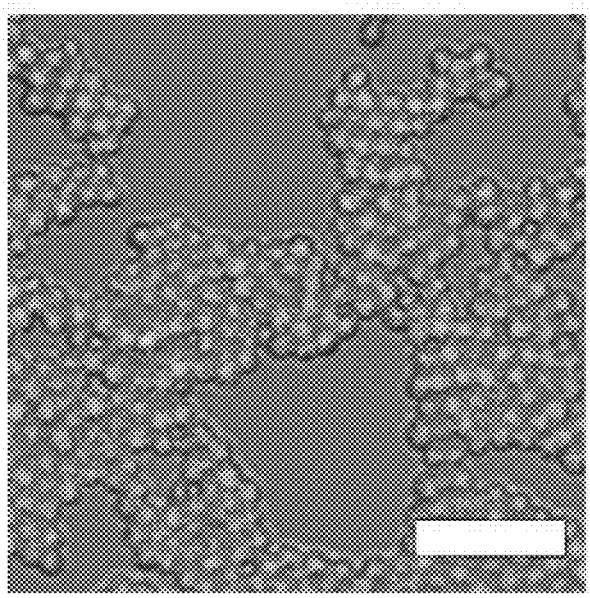
Figure 3D:
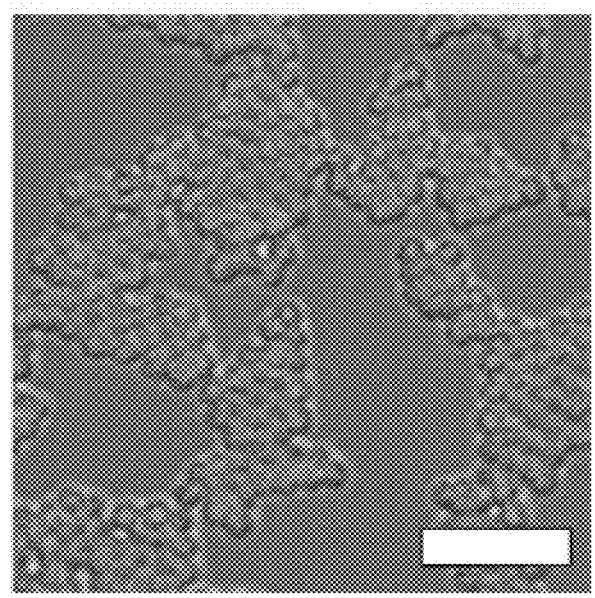
Figures 9A, 9B:
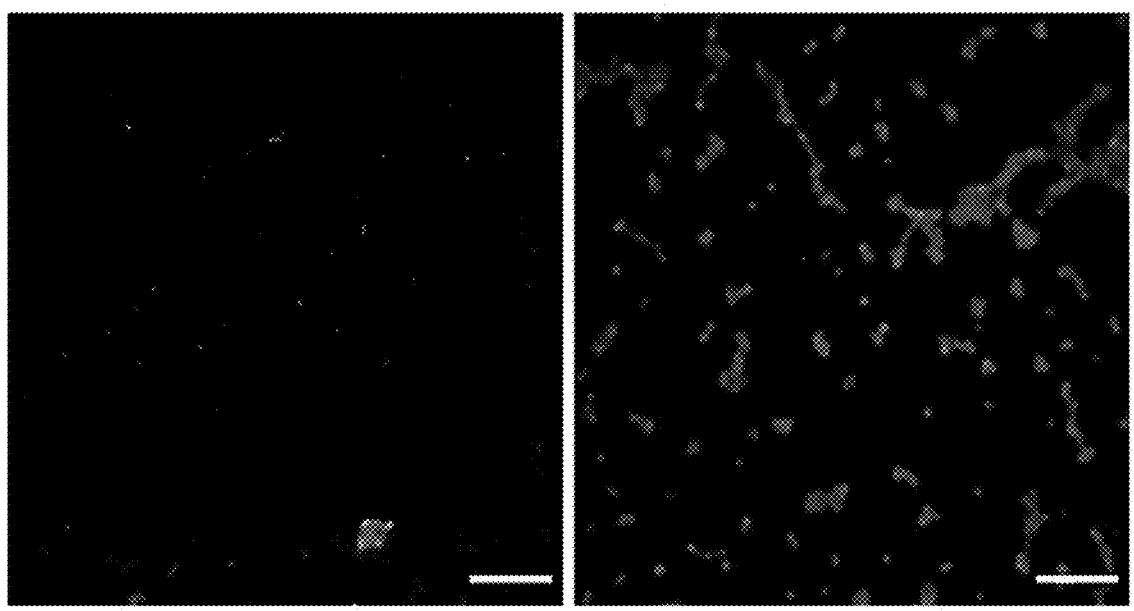
FIGS. 9A-9B show fluorescence images of *S. aureus* cultured in either standard media (FIG. 9A) or iron-challenged media (FIG. 9B), then treated with Ga-PpIX (bar=10 µm). The latter shows stronger fluorescence intensities, indicating the expression of CSHRs under iron-challenged conditions.

These assumptions were tested by incubating bacteria with Ga-PpIX at a fixed concentration (7.3 µM) for 15 to 60 minutes. *S. aureus* was strongly and uniformly labelled within the first 15 minutes, with fluorescence remaining constant over time (FIG. 3A). In contrast, labelling of *Y. enterocolitica* was initially weak and heterogeneous, gradually increasing over a 60-minute period (FIGS. 3B-D). Specificity of Ga-PpIX as a substrate for direct hemin uptake by *S. aureus* was also established by competitive inhibition with equimolar hemin (see below). We note that hemin (and Ga-PpIX) uptake by *S. aureus* is activated by the ferric uptake regulator (fur) gene, which increases Isd expression upon metal deprivation. Fur-dependent expression of high-affinity CSHRs was confirmed by comparing *S. aureus* cultured in standard and iron-limited conditions, with modest levels of Ga-PpIX uptake observed by the former but dramatically higher uptake by the latter (FIG. 9, Tables 3 and 4). Iron-limited conditions are relevant from a clinical perspective, as the body withdraws all available sources of iron during infection, which induces pathogens to expression various iron acquisition systems including CSHRs.

Figure 4:
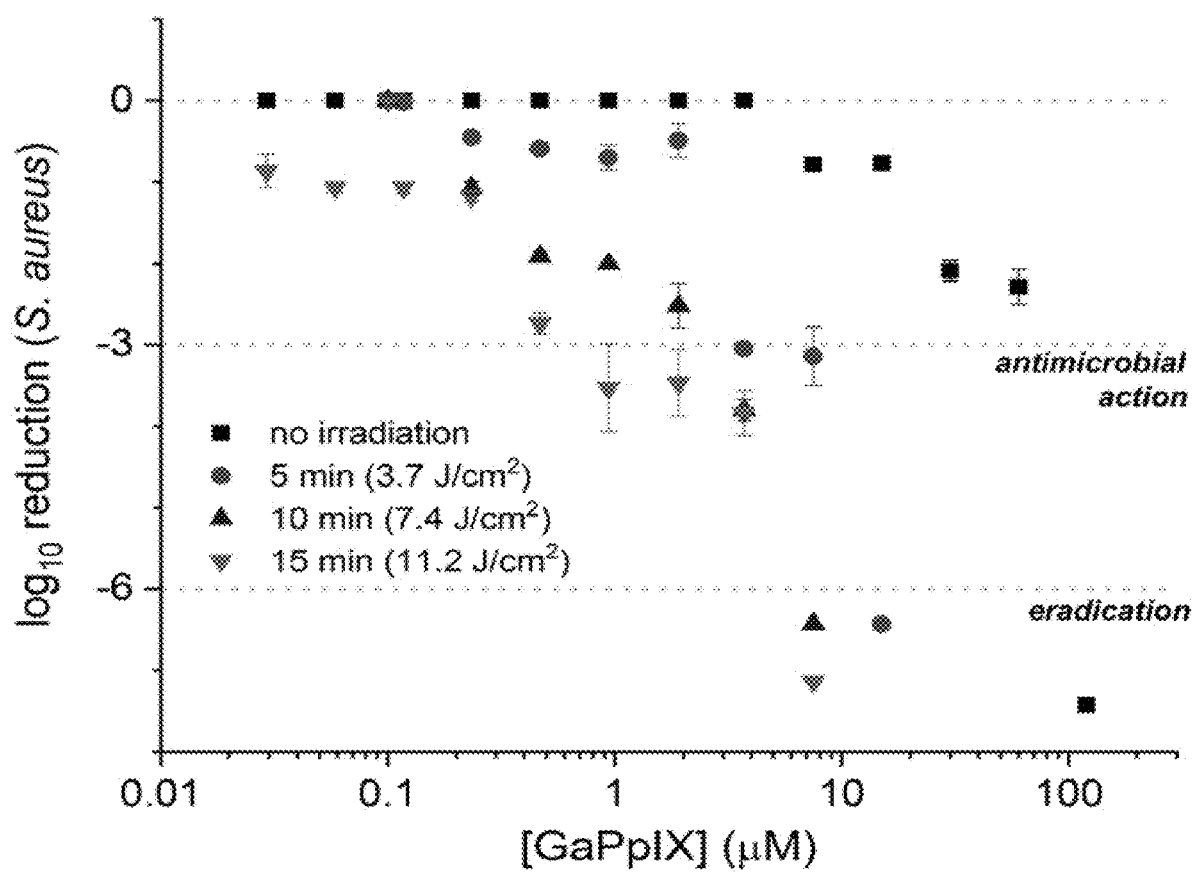
FIG. 4 shows normalized survival plots of *S. aureus* as a function of Ga-PpIX concentration and exposure time to 406-nm light from a compact fluorescent light bulb (CFL; 12.4 mW/cm$^2$). Bacteria were plated after irradiation and incubated at 37° C. for 20 h. Antimicrobial action and eradication correspond to 3- and 6-log reductions in cfu/mL, respectively.

Next, Ga-PpIX was evaluated as a fast-acting aPDI agent against a laboratory strain of *S. aureus* (PCI 1203; ATCC 10537). Studies were performed in the context of topical antiseptics using blue light from a 20-W CFL bulb ($\lambda_{max}$ 406 nm, 12.4 mW/cm$^2$), bypassing issues of transmission through tissue and the risk of DNA damage induced by UV irradiation. Gratifyingly, we found this inexpensive light source to be sufficient for potent aPDI against planktonic *S. aureus*. The aPDI activity of Ga-PpIX is remarkably rapid, with >99.9% reduction at 470 nM after 15 minutes of irradiation and total eradication (>6 log reduction) at 7.5 µM, a 128 and 16-fold increase in potency relative to Ga-PpIX dark toxicity (FIG. 4 and Table 1). Comparable aPDI activity within 5 minutes could be achieved when using higher concentrations (3.75 and 15 µM for 3- and 6-log reductions, respectively). The aPDI properties of Ga-PpIX were compared against PpIX, whose photosensitizer activities are well known and whose optical profile is similar to that of Ga-PpIX (FIG. 2). PpIX had weaker aPDI activity (1.1 µM) as well as higher dark toxicity (36 µM), thereby establishing Ga-PpIX as a superior aPDI agent.

TABLE 1 aPDI activity of Ga-PpIX and PpIX against various staphylococcal strains Antimicrobial activity, in µM (minimum 3-log CFU reduction)

| Exposure | Ga- | potenc | PpIX | potenc | TMPy | potenc |
|---|---|---|---|---|---|---|
| *S. aureus* (PCI 1203; ATCC 10537) | | | | | | |
| 0 min (dark) | >60 | — | 36 | — | <7.4 | — |
| 5 min | 3.75 | >16x | — | — | 0.92 | <8x |
| 15 min | 0.47 | >128x | 1.1 | 32x | 0.23 | <32x |
| MRSA (USA200), clinical isolate NRS 383 | | | | | | |
| 0 min (dark) | 36.3 | — | 36.3 | — | | |
| 15 min | 1.1$^c$ | 32x | 1.1$^c$ | 32x | | |
| MRSA (USA500), clinical isolate NRS 385 | | | | | | |
| 0 min (dark) | >146$^d$ | — | >146$^d$ | — | | |
| 15 min | 4.6 | >32x | 18.3 | >8x | | |
| MRSA (USA700), clinical isolate NRS 386 | | | | | | |
| 0 min (dark) | >146$^d$ | — | >146$^d$ | — | | |
| 15 min | 4.6 | >32x | 36.3 | >4x | | |

TABLE 1-continued aPDI activity of Ga-PpIX and PpIX against various staphylococcal strains
Antimicrobial activity, in μM (minimum 3-log CFU reduction)

| Exposure | Ga- | potenc | PpIX | potenc | TMPy | potenc |
|---|---|---|---|---|---|---|
| MRSA (USA800), clinical isolate NRS 387 | | | | | | |
| 0 min (dark) | 73 | — | 146 | — | | |
| 15 min | 1.1 | 64x | 9.1 | 16x | | |
| S. epidermis (ATCC 155) | | | | | | |
| 0 min (dark) | 146 | — | >146[d] | — | | |
| 15 min | 0.57 | 256x | 4.6 | >32x | | |

[a]Exposure to 20-W CFL (406 nm, 12.4 mW/cm$^2$). Fluences for 5- and 15-min irradiation times are 3.7 and 11.2 J/cm$^2$, respectively.
[b]Relative to dark toxicity (0 min exposure).
[c]Eradication (>6 log reduction) observed at 2.3 μM for Ga-PpIX and 4.6 μM for PpIX.
[d]Bactericidal activity did not exceed 3 log reduction at the highest level tested.

As an extra measure, we compared the activity of Ga-PpIX to that of TMPyP, a tetracationic porphyrin shown by Maisch and coworkers to be a fast-acting aPDI agent, albeit one with indiscriminate uptake (Eichner, A. et al., *Photochem. Photobio. Sci.* 2013, 12, 135-147). TMPyP was administered under the same conditions as before and could produce aPDI activity at half the concentration of Ga-PpIX (0.23 μM) but also had much stronger dark toxicity (<7.4 μM), resulting in a lower relative potency with negative implications for clinical use. In this context, it is worth mentioning a very recent report in which 5 μM TMPyP and blue-light irradiation was shown to produce aPDI at power densities as low as 0.13 mW/cm$^2$, meaning that some level of photosensitization is possible even with ambient lighting.

To demonstrate its therapeutic potential, Ga-PpIX was also deployed against four clinical isolates of MRSA known to exhibit resistance to various antibiotics including macrolides, aminoglycosides, lincosamides, and fluoroquinolones. In all cases, we observed potent aPDI with bactericidal activities at 1-5 μM (Table 1). The consistent response to Ga-PpIX treatment is encouraging, as variable efficacy between strains is a known problem in antimicrobial photodynamic therapy (Nakonieczna, J. et al., *Photodiagn. Photodyn. Ther.* 2012, 9, 359-361). Ga-PpIX was even more effective against a clinical isolate of *S. epidermidis* from a skin lesion (a common factor in biofilm-associated infections), with bactericidal activity at 570 nM and >6 log reduction at 1.1 μM. Again, a parallel study with PpIX indicated the latter had similarly rapid action, but was less potent than Ga-PpIX. We note that PpIX is already approved as a photosensitizer for topical treatment of several skin diseases, but its utility is limited by poor photostability.

Figure 5A:
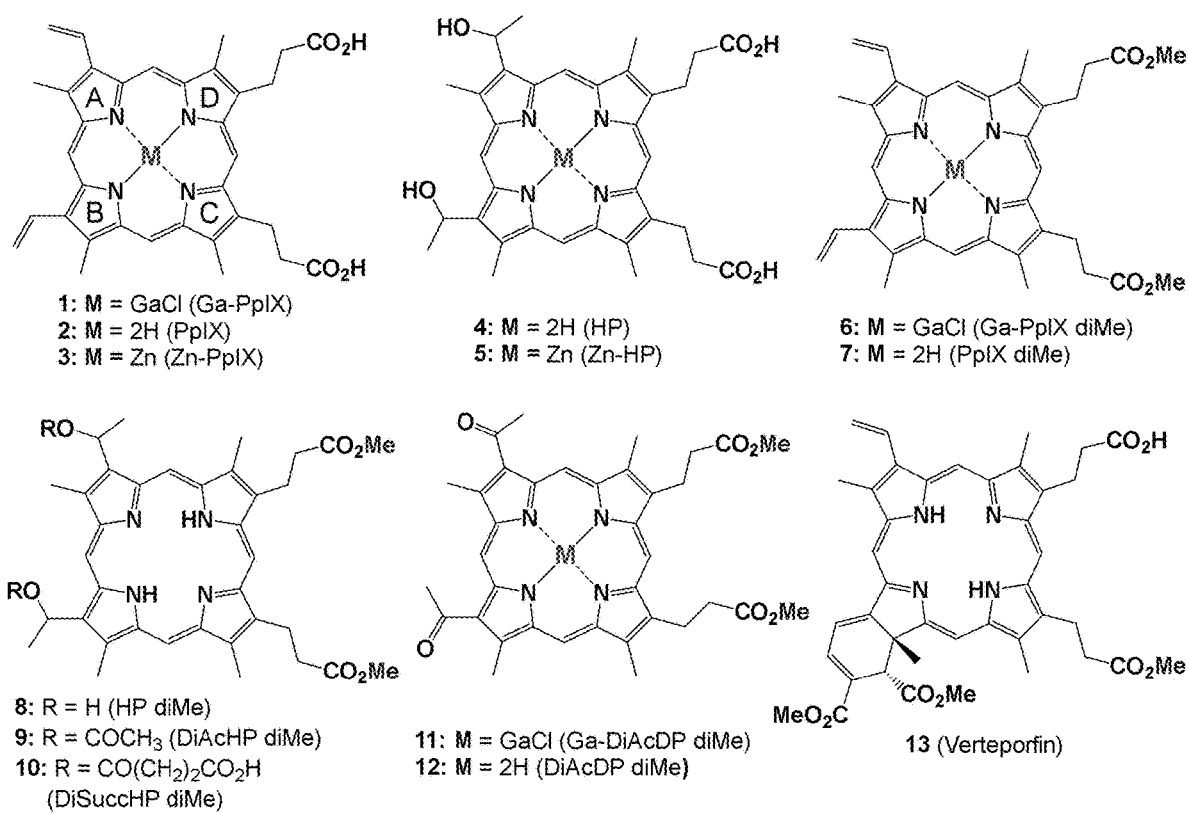
FIG. 5A depicts the structures of PpIX derivatives 1-13.
Figure 5B:
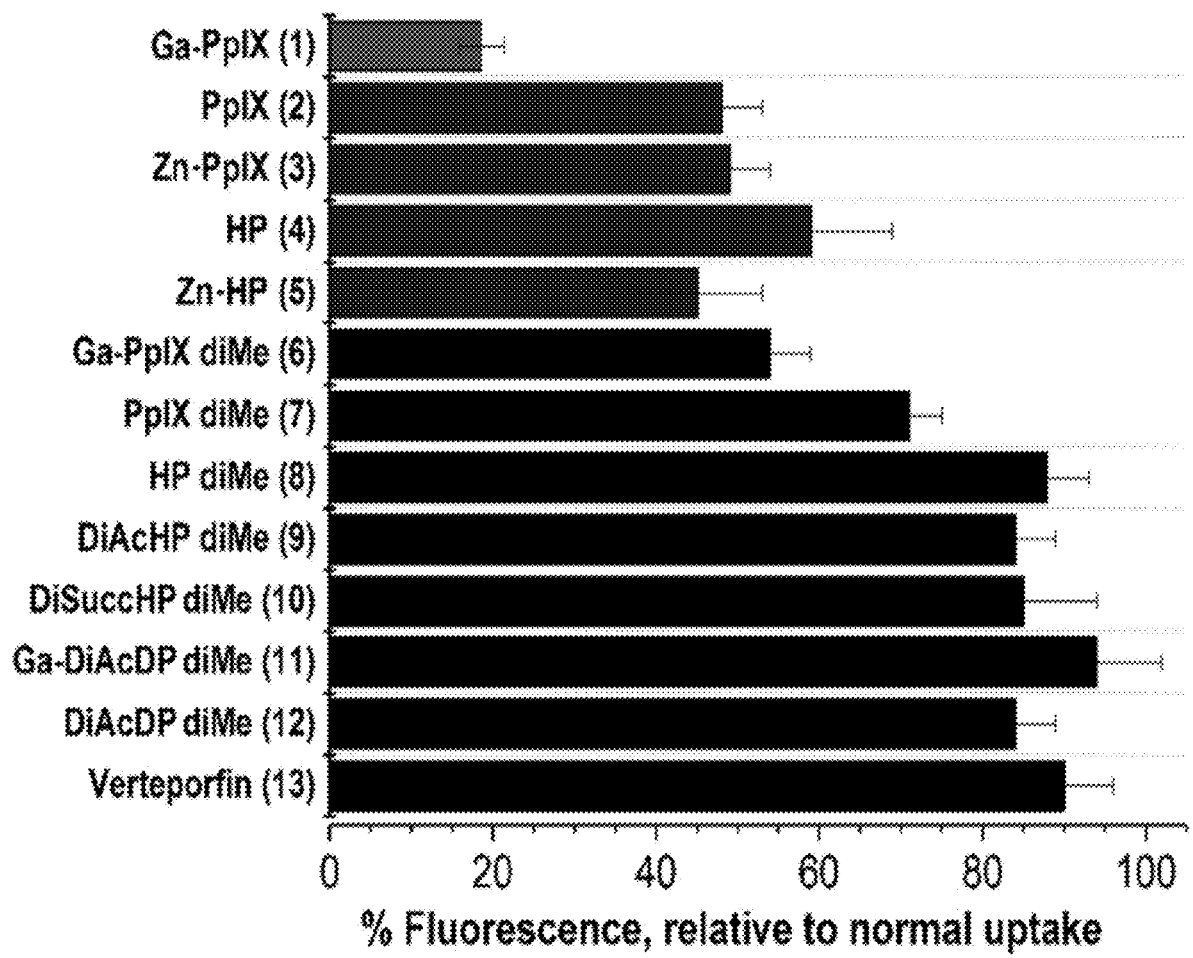
FIG. 5B shows competitive uptake of PpIX derivatives 1-13 by *S. aureus* (PCI 1203) versus one equivalent of hemin (15 min co-exposure). Values are relative to uptake in the absence of hemin.

To elucidate the relevant structural features for the specific uptake of Ga-PpIX by *S. aureus*, we performed a competitive uptake assay using one equivalent of hemin against Ga-PpIX, PpIX, and eleven other fluorescent PpIX derivatives, with evaluation by fluorescence microscopy after 15 minutes of co-incubation (FIG. 5 and Table 4). These studies were partly guided by insights taken from the X-ray structures of hemin and Ga-PpIX within the binding pocket of IsdH: (i) coordination of the metal center by an apical tyrosine residue; (ii) the flanking of vinyl groups on pyrrole rings A and B against nearby aromatic residues; and (iii) the extension and presumed hydration of the propionyl groups (rings C and D) outside of the binding pocket.

The competitive uptake assay produced three important observations: (i) the uptake of Ga-PpIX (1), an ionic complex, was strongly affected by competition with hemin, with greater than 80% reduction in fluorescence; (ii) the uptake of PpIX (2), Zn-PpIX (3), HP (4), and Zn-HP (5) were slower than 1 but still moderately affected by hemin; and (iii) uptake of dimethyl diesters 6-8 (derived from 1, 2, and 4), tetraesters 9 and 10 (di-O-acetyl and -succinyl derivatives of 8), diacetyldeuteroporphyrins (DiAcDP) 11 and 12, and verteporfin 13 were all less affected by hemin, several of which are essentially independent of CSHR activity. The first two insights indicate that the Isd proteins of *S. aureus* have stronger affinity for ionic PpIX derivatives and weaker affinity for non-ionic derivatives, with nonspecific uptake pathways being more significant in the latter case. This was confirmed by using *S. aureus* with low Isd expression (cultivation in Fe-replete conditions), which essentially neutralized the impact of hemin on the uptake of 1 and 2 (Table 5). We therefore consider the ionic character of Ga-PpIX to be important for rapid uptake and the free propionyl groups to be important for specific uptake, as their esterification increases lipophilicity and contributes toward loss of specificity.

Figure 6:
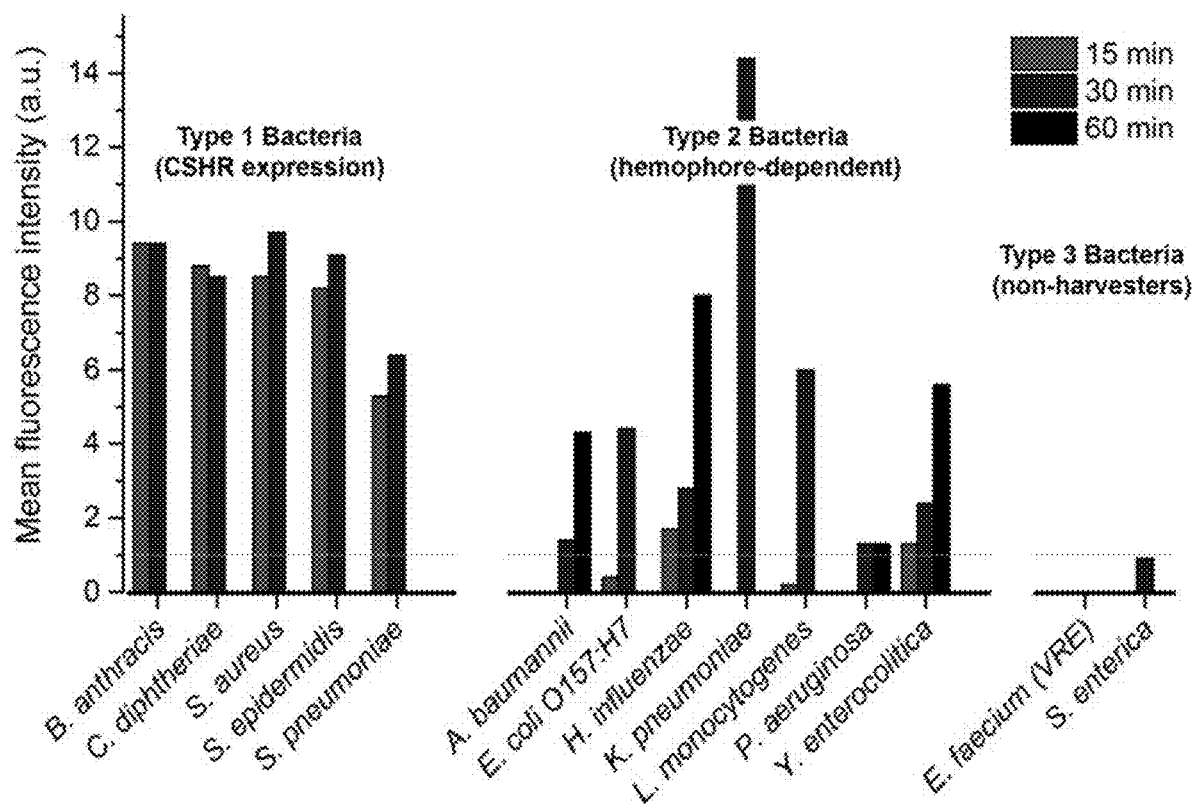
FIG. 6 shows GaPpIX uptake by representative bacteria, classified into three types based on rates of saturation. Type I bacteria include those known to express CSHRs, enabling rapid and specific uptake of GaPpIX. A threshold of significance defined by the autofluorescence of *S. enterica typhimurium* (negative control) is marked in grey.

Finally, the scope of rapid aPDI delivery via direct hemin uptake was investigated by evaluating the relative uptake rates of Ga-PpIX against a panel of 14 common bacterial pathogens (FIG. 6 and Table 2). Several species were found to have Ga-PpIX uptake profiles similar to *S. aureus* (Type 1), while other pathogens exhibited a delay in Ga-PpIX uptake by 15 minutes or more (Type 2); two were determined to be insensitive to hemin (Type 3). Type 1 pathogens are exclusively Gram-positive, and their rapid uptake of Ga-PpIX is commensurate with current information on the expression of CSHRs. Staphylococci and *B. anthracis* produce high levels of Isd proteins as previously mentioned, and *C. diphtheriae* expresses HtaA and B, membrane-anchored proteins that function at the initial stages of hemin acquisition. Type 2 pathogens include both Gram-positive and -negative species, all of which are known to rely on hemophores for hemin acquisition (Table 2). It is worth noting that Type 3 pathogen *S. enterica typhimurium* is autofluorescent, which provides a convenient threshold of significance for the Ga-PpIX uptake study.

TABLE 2

Bacterial pathogens featured in FIG. 6[a]

| Bacteria, by classification | Culture conditions | Hemin acquisition proteins[c] |
|---|---|---|
| Type 1 (CSHR expressing) | | |
| *Bacillus anthracis* (Ames 35 strain) | Tryptic soy | Isd (C, E, X1, X2), BslK, Hal |
| *Corynebacterium diphtheriae* (5159) | Brain-heart infusion | HmuT, Hta (A, B) |
| *Staphylococcus aureus* (PCI 1203) | Tryptic soy | Isd (A, B, C, E, H) |
| *Staphylococcus epidermidis* (ATCC 155) | Tryptic soy | Isd (A, B, C, E, H) |
| *Streptococcus pneumoniae* (CDC CS111) | Brain-heart infusion[b] | unassigned |

TABLE 2-continued

Bacterial pathogens featured in FIG. 6[a]

| Bacteria, by classification | Culture conditions | Hemin acquisition proteins[c] |
|---|---|---|
| Type 2 (hemophore producing) | | |
| *Acinetobacter baumannii* (DSM 6974) | Nutrient broth | unassigned |
| *Escherichia coli* O157:H7 (CDC EDL 933) | Tryptic soy | ChuA, Hma, ShuA |
| *Klebsiella pneumoniae* (S 389) | Nutrient broth | unidentified |
| *Listeria monocytogenes* (J0161) | Brain-heart infusion | HupC, Hbp2/SvpA |
| *Haemophilus influenzae* (AMC 36-A-5) | Gonococcal medium[b] | Hgp (A, B, C), Hup, HxuC |
| *Pseudomonas aeruginosa* (PAO1-LAC) | Luria-Bertani | Has (A, R), PhuR |
| *Yersinia enterocolitica* (WA-314) | Luria-Bertani | HemR |
| Type 3 (non-harvesters) | | |
| *Enterococcus faecium* (VRE) | Brain-heart infusion | — |
| *Salmonella enterica typhimurium* (LT2) | Nutrient broth | — |

[a]Details taken from the following references unless otherwise noted (Allen, CE, et al., *J. Bacteriol.* 2009, 191, 2638-2648; Romero-Espejel, ME, et al., Metallomics 2013, 5, 384-389; McConnell, MJ, et al, FEM Microbiol. Rev. 2013, 37, 130-155).
[b]5% $CO_2$ atmosphere.
[c]Abbreviations: Bsl, *B. anthracis* S-layer; Chu, *E. coli* heme utilization; Hal, heme-acquisition leucine-rich; Has, heme acquisition system; Hbp, hemin binding protein; Hem, hemin receptor; Hgp, hemoglobin/haptoglobin binding protein; Hma, heme acquisition protein; Hmu, hemin uptake; Hta, hemin transport; Hup, heme uptake; Hxu, hemopexin uptake; Isd, iron-regulated surface determinant; Phu, *Pseudomonas* heme uptake; Shu, Shigella heme uptake; Svp, surface virulence-associated protein.

Antibacterial Activity Assay Procedure and Results

Antibacterial activity assay general protocol: Used LED light to test conditions. Bacteria were grown in TS broth, followed by 3 mM bipyridine in TS broth until log phase. Bacteria were then diluted with PBS, to OD 0.1 (~10^) and then to ~10^7 cfu/mL. 100 uL of bacteria were placed in 96 well plates with the appropriate GaPpIX concentration. 2× serial dilutions were then done to obtain other GaPpIX concentrations. Each concentration was done in triplicate. Bacteria were left incubating and irradiating for different amount of times at different light powers or left in the dark. 10× Serial dilutions were done and bacteria were plated for colony counting using the drop-plate technique. Colonies were counted after 24 hours. As reported herein, a 3-log reduction equals measurable antimicrobial action; a 6-log reduction equals total eradication.

Example #AVM-3-33: GaPpIX against *S. aureus*. Results: 59 nM for 3-log reduction and 235 nM for 6-log reduction, wherein 3-log reduction equals measurable antimicrobial action; 6-log reduction equals total eradication.

Example #AVM-3-34A: GaPpIX against MRSA383. Results: 59 nM for 3-log reduction and 118 nM for 6-log reduction.

Example #AVM-3-34B: GaPpIX against MRSA385. Results: 89 nM for 3-log reduction and 470 nM for 6-log reduction.

Example #AVM-3-34C: GaPpIX against MRSA386. Results: 118 nM for 3-log reduction and 235 nM for 6-log reduction.

Example #AVM-3-34D: GaPpIX against MRSA387. Results: 59 nM for 3-log reduction and 1900 nM for 6-log reduction.

Example #AVM-3-35: TMPyP against *S. aureus*. Results: 235 nM for 3-log reduction and 940 nM for 6-log reduction.

Example #AVM-3-36: PpIX against *S. aureus*. Results: 940 nM for 3-log reduction and 1900 nM for 6-log reduction.

Enhancement of Antibacterial Effects with the Addition of Silver Nanoparticles (AgNP, 10 or 40 nm in Size).

Stock solution preparation (AVM-3-36, 10 nm AgNP). Prepared a solution of (AVM-2-273) GaPpIX-apoHb 1 mg/mL in MP H2O, deaerated. Took 10 mL of 10 nm AgNPs, centrifuged at 900 G for 5 min (Beckman, 3100 RPM), took supernantant and added 200 uL of GaPpIXHb. After overnight, centrifuged 3000 RPM g for 5 minutes (Beckman). Took supernantant and centrifuged using a 100 K CentriCon tube at 4000 RPM for 5 minutes, 3×. Added 15 mM borate buffer to NPs. Based on calibration curve, the stock solution is 1.94 ug/mL AgNP, so stock: 79 μg/mL AgNP, 10.37 μg/mL GaPpIXHb, 0.446 μg/mL GaPpIX (refer to AVM-2-293A and AVM-3-3).

Stock solution preparation (AVM-3-37, 40 nm AgNP). Prepared a solution of (AVM-2-273) GaPpIX-apoHb 1 mg/mL in MP H2O, deaerated. Took 7 mL of 40 nm AgNPs, centrifuged at 900 G for 5 min (Beckman, 3100 RPM), took supernantant and added 200 uL of GaPpIXHb. After overnight, centrifuged 5700 RPM g for 20 minutes (Beckman). Added 15 mM borate buffer to NPs. Based on calibration curve (dilution of 10 uL+200 buffer, total 210 uL) and Bradford assay: the stock is 133 μg/mL AgNP, 27.5 μg/mL GaPpIXHb, 1.1 μg/mL GaPpIX (refer to AVM-2-293B for AgNPs calibration curve and AVM-3-10B for Bradford Assay).

The following antibacterial activity measurements were assayed in the presence of AgNP.

Example #AVM-3-38A: GaPpIX against *S. aureus* with 10 nm AgNP. Results: 22 nM for 3-log reduction and 27 nM for 6-log reduction, wherein 3-log reduction equals measurable antimicrobial action; 6-log reduction equals total eradication.

Example #AVM-3-39A: GaPpIX/10 nm HbAgNP against MRSA383. Results: 27 nM for 3-log reduction and 79 nM for 6-log reduction, wherein 3-log reduction equals measurable antimicrobial action; 6-log reduction equals total eradication.

Example #AVM-3-39B: GaPpIX/10 nm HbAgNP against MRSA385. Results: 27 nM for 3-log reduction and 109 nM for 6-log reduction, wherein 3-log reduction equals measurable antimicrobial action; 6-log reduction equals total eradication.

Example #AVM-3-39C: GaPpIX/10 nm HbAgNP against MRSA386. Results: 79 nM for 3-log reduction and 158 nM for 6-log reduction, wherein 3-log reduction equals measurable antimicrobial action; 6-log reduction equals total eradication.

Example #AVM-3-39D: GaPpIX/10 nm HbAgNP against MRSA387. Results: 43 nM for 3-log reduction and 218 nM for 6-log reduction, wherein 3-log reduction equals measurable antimicrobial action; 6-log reduction equals total eradication.

In conclusion, CSHR-expressing pathogens such as *S. aureus* can be targeted for rapid aPDI, using nanomolar Ga-PpIX and an inexpensive CFL source with irradiation times of 15 minutes or less. Ga-PpIX has excellent potential as a topical antiseptic, given its previously established reputation for low in vitro and in vivo dark toxicity, and is a more potent and possibly more robust alternative to the clinically relevant PpIX. A structure-based competition assay reveals the importance of ionic character and the presence of free propionyl units in the specific uptake of Ga-PpIX by *S. aureus*. Lastly, the rapid uptake of Ga-PpIX by CSHR-expressing bacteria suggests opportunities to design molecular conjugates for the targeted delivery of other antimicrobial agents.

Experimental Section

Hemin chloride and all reagents were obtained from commercial sources, and used as received unless otherwise noted. Dimethyl sulfoxide (DMSO) was distilled over $CaH_2$ under reduced pressure. Deionized water was obtained from an ultrafiltration system (Milli-Q, Millipore) with a resistivity >18 MΩ·cm, and passed through a 0.22-μm filter to remove particulate matter. Absorption spectra were collected on a Varian Cary50 spectrometer; fluorescence emission data were collected on a Cary Eclipse fluorimeter with a gate time of 5 ms. $^1$H NMR spectra were obtained in $CDCl_3$ or DMSO-$d_6$ using a Varian 800-MHz spectrometer; all chemical shifts (δ) reported in ppm.

Fluorescence images were acquired in air using an upright microscope with Hg lamp and filter set for $\lambda_{em}$>570 nm (Olympus BX51, U-MWG2), or using a laser scanning confocal microscope with 488 nm excitation and a bandpass filter between 505 and 605 nm (Olympus FV1000, DM405/488; BA505-605). Care was taken to minimize UV or laser exposure time to less than 5 seconds to avoid bleaching of molecules. Fluorescence data analyses were performed in triplicate using Image J 1.47v, based on mean pixel intensities from labelled bacteria (8-bit format).

Synthesis of PpIX and Related Derivatives.

Ga-PpIX (1) (Bohle, D S, et al., *Inorg. Chem.* 2012, 51, 10747-10761), Zn-PpIX (3) (Clark, E. et al, *Inorg. Chem.* 2017, 56, 4584), hematoporphyrin (HP; 4) and Zn-HP (5) (Xu, S. et al., *Chin. J. Appl. Chem.* 2011, 28, 657-661), and PpIX dimethyl diester (7)(Byrne, C J. Et al, *Tetrahedron Lett.* 1988, 29, 1421-1424) were synthesized from PpIX (2) as previously described. HP dimethyl diester (8) and di-O-acetyl- and di-O-succinyl-HP dimethyl diester (9, 10) were synthesized from HP as previously described (Bonnett, R, et al., *J. Chem. Soc., Perkin Trans.* 1981, 1, 3135-4140). PpIX 2 was prepared by warming hemin chloride (500 mg, 0.77 mmol) to 60° C. in formic acid (19 mL), followed by the addition of iron powder (516 mg, 9.24 mmol) in two separate portions with magnetic stirring (Erdman, J G, et al., *J. Am. Chem. Soc.* 1956, 78, 5844-5847). A condenser was attached and the reaction mixture was heated to reflux (125° C.) for 30 minutes, then cooled to room temperature and filtered. The filtrate was treated with 300 mL of saturated aqueous sodium acetate, then centrifuged at 8300 g for 15 minutes to collect the product. The retentate was washed with water three times then dried in air, yielding 2 as a brown solid (390 mg, 91% yield). UV/vis $A_{max}$ (MeOH): 405, 504, 539, 574, 629 nm. $^1$H NMR (DMSO-$d_6$, 800 MHz): δ 3.17 ($CH_2$, 4H, m), 3.61 (methyl, 3H, s), 3.64 (methyl, 3H, s), 3.74 (methyl, 3H, s), 3.75 (methyl, 3H, s), 4.34 ($CH_2$, 4H, m), 6.22 (vinyl, 2H, dd, J=8, 16 Hz), 6.46 (vinyl, 2H, dd, J=8, 16 Hz), 8.52 (vinyl, 2H, m), 10.28 (2H, s), 10.31 (1H, s), 10.35 (1H, s).

Ga(III)-PpIX dimethyl diester 6 was synthesized by dissolving diester 7 (10 mg, 0.017 mmol) in anhydrous DMF (3 mL), followed by addition of excess anhydrous $GaCl_3$ (50 mg, 0.28 mmol) in a glass microwave vessel. The reaction mixture was heated to 170° C. under microwave conditions (45 W) for 10 minutes, and monitored by UV-vis spectroscopy for the disappearance of two bands at 500 and 630 nm. After Ga insertion was considered to be complete, the reaction mixture was diluted with dichloromethane (10 mL) and washed with water (10 mL) three times. The organic layer was dried with sodium sulfate and concentrated to yield 6 as a dark red solid (8 mg, 68% yield). Purity was confirmed by HPLC: RP-C18 column, 0.1% aq TFA). UV/vis $A_{max}$ (MeOH): 404, 537, 576 nm. $^1$H NMR (DMSO-$d_6$, 800 MHz): δ 3.17 ($CH_2$, 4H, t, J=6.6 Hz), 3.55 ($OCH_3$, 6H, s), 3.74 (methyl, 3H, s), 3.77 (methyl, 3H, s), 3.87 (methyl, 3H, s), 3.88 (methyl, 3H, s), 4.52 ($CH_2$, 4H, t, J=6.6 Hz), 6.31 (vinyl, 2H, dd, J=8, 16 Hz), 6.55 (vinyl, 2H, dd, J=8, 16 Hz), 8.54 (vinyl, 2H, m), 10.50 (1H, s), 10.55 (1H, s), 10.56 (1H, s), 10.63 (1H, s).

Ga(III) diacetyldeuteroporphyrin (diAcDP) dimethyl diester 11 was synthesized by dissolving diAcDP diester 12 (6 mg, 0.010 mmol) in anhydrous DMF (3 mL), followed by addition of excess anhydrous $GaCl_3$ (48 mg, 0.27 mmol) in a glass microwave vessel. The reaction mixture was heated to 170° C. under microwave conditions (45 W) for 10 minutes, and monitored by UV-vis spectroscopy as described above until Ga insertion was considered complete. The reaction mixture was diluted with dichloromethane (10 mL) and washed with water (10 mL) three times. The organic layer was dried with sodium sulfate and concentrated to yield 11 as a dark red solid (5 mg, 68% yield), with purity confirmed by HPLC (RP-C18 column, 0.1% aq TFA). UV/vis $A_{max}$ (MeOH): 410, 542, 582 nm. $^1$H NMR ($CDCl_3$, 800 MHz): δ 3.27 ($CH_2$, 4H, m), 3.35 ($OCOCH_3$, 6H, s), 3.59 (methyl, 3H, s), 3.60 (methyl, 3H, s), 3.66 ($OCH_3$, 6H, s), 3.91 (methyl, 3H, s), 3.93 (methyl, 3H, s), 4.35 ($CH_2$, 4H, m), 9.94 (1H, s), 10.07 (1H, s), 10.70 (1H, s), 10.92 (methine, 1H, s).

3,8-Diacetyldeuteroporphyrin dimethyl diester (12) was synthesized by dissolving HP dimethyl diester 8 (20 mg, 0.032 mmol) in dry dichloromethane (3.2 mL), then treatment with activated 4A molecular sieves (20 mg) and Dess-Martin periodinane (30 mg, 0.07 mmol) at room temperature under an argon atmosphere. The reaction mixture was stirred for two hours, then diluted with dichloromethane (10 mL) and aqueous sodium thiosulfate (10 mL) and allowed to stir for 30 min, followed by saturated aqueous sodium bicarbonate (10 mL) with additional stirring for 10 minutes. The organic layer was separated, dried with sodium sulfate, then concentrated to dryness to yield 12 as a dark brown solid (18 mg, 90% yield). Purity confirmed by HPLC (RP-C18 column, water with 0.1% TFA). UV/vis $A_{max}$ (MeOH): 416, 512, 548, 580, 641 nm. $^1$H NMR: ($CDCl_3$, 800 MHz): δ 3.28 ($CH_2$, 4H, m), 3.50 ($OCOCH_3$, 6H, s), 3.54 (methyl, 3H, s), 3.57 (methyl, 3H, s), 3.68 ($OCH_3$, 6H, s), 3.80 (methyl, 3H, s), 3.86 (methyl, 3H, s), 4.33 ($CH_2$, 4H, m), 9.82 (1H, s), 9.86 (1H, s), 10.60 (1H, s), 10.75 (1H, s).

Microbiological Culture Conditions.

All bacterial strains were cultured at 37° C. in an aerobic atmosphere unless otherwise noted. Bacterial suspensions were typically incubated for up to 16 hours until an optical density of 1.0 was achieved at 600 nm. Bacterial counts were estimated in units of cfu/mL by plating serial dilutions onto agar plates, followed by incubation for 16 hours at 37° C. Iron-challenged conditions were typically achieved by first growing the bacteria in standard (iron-replete) media (see Table 2), then harvesting and resuspending in media containing 3 mM 2,2'-bipyridine. Further details and variations on iron-deficient culture conditions are provided in Supporting Information.

Bacterial Uptake Assay of Ga-PpIX and Related Derivatives.

Bacteria were cultured and assayed in iron-deficient media unless otherwise noted. A stock solution of Ga-PpIX (14.6 µM) was prepared by dispersing 5 mg in 1 mL of 10% DMSO in PBS for 10 minutes in an ultrasonic cleaning bath protected from light, followed by filtration and 10× dilution in PBS just prior to use. Bacterial suspensions (0.5 mL) were treated with freshly prepared solutions of PpIX derivatives for specified periods (5-15 min), then harvested by centrifugation at 5.2 g for 5 minutes, redispersed twice in 0.5 mL deionized water, and centrifuged a third time. A 10-µL aliquot of concentrated bacteria was deposited onto a glass slide and dried in air for 20 min, then imaged by fluorescence microscopy as described above. For details on fluorescence image processing and quantitative analysis, see Supporting Information.

Competitive Hemin Uptake Assay.

S. aureus (PCI 1203; ATCC 10537) was first cultured in standard TS broth, then in media containing 3 mM bipyridine. Bacteria were pelleted and washed with PBS buffer three times, then resuspended to a final concentration of $10^8$ cfu/mL. Stock solutions of hemin and PpIX derivatives 1-13 were prepared at initial concentrations of 292 µM; hemin and fluorescent PpIX solutions were mixed in a 1:1 ratio (0.5 mL), then added to 0.5 mL of bacterial suspension and allowed to sit for 15 min at room temperature. For control studies, hemin or fluorophore solutions were substituted with PBS to maintain constant concentration. Bacteria were harvested and washed as described above, then evaluated by fluorescence microscopy for relative uptake efficiency.

Antimicrobial Photodynamic Inactivation (aPDI).

A 20-W compact fluorescent lightbulb (CFL; Sunlite SL20/BLB) housed in an ellipsoidal reflector dome was used for aPDI, at an emission wavelength at 406 nm and a mean power density of 12.4 mW/cm$^2$ (after applying a 408-nm shortpass filter). Antimicrobial assays were performed on planktonic bacteria at $10^7$ cfu/mL with variable exposure times to CFL irradiation, followed by plating on agar and incubation at 37° C. In a typical experiment, bacterial suspensions were transferred into 96-well plates then treated with 100-µL aliquots of Ga-PpIX or PpIX solution, with final concentrations ranging from 320 to 0.31 µg/mL, followed immediately with CFL irradiation for 5 to 15 minutes. The irradiated bacteria were plated onto agar in serial tenfold dilutions ($10^7$-$10^1$ cfu/mL); controls included one set of wells without photosensitizer, and one set of wells with photosensitizer but without 15 min irradiation, prior to plating (dark toxicity). Bacterial counts were determined by the drop-plate method using TS-agar plates, and reported in colony-forming units per milliliter (cfu/mL).

Photophysical Measurements

Figure 7:
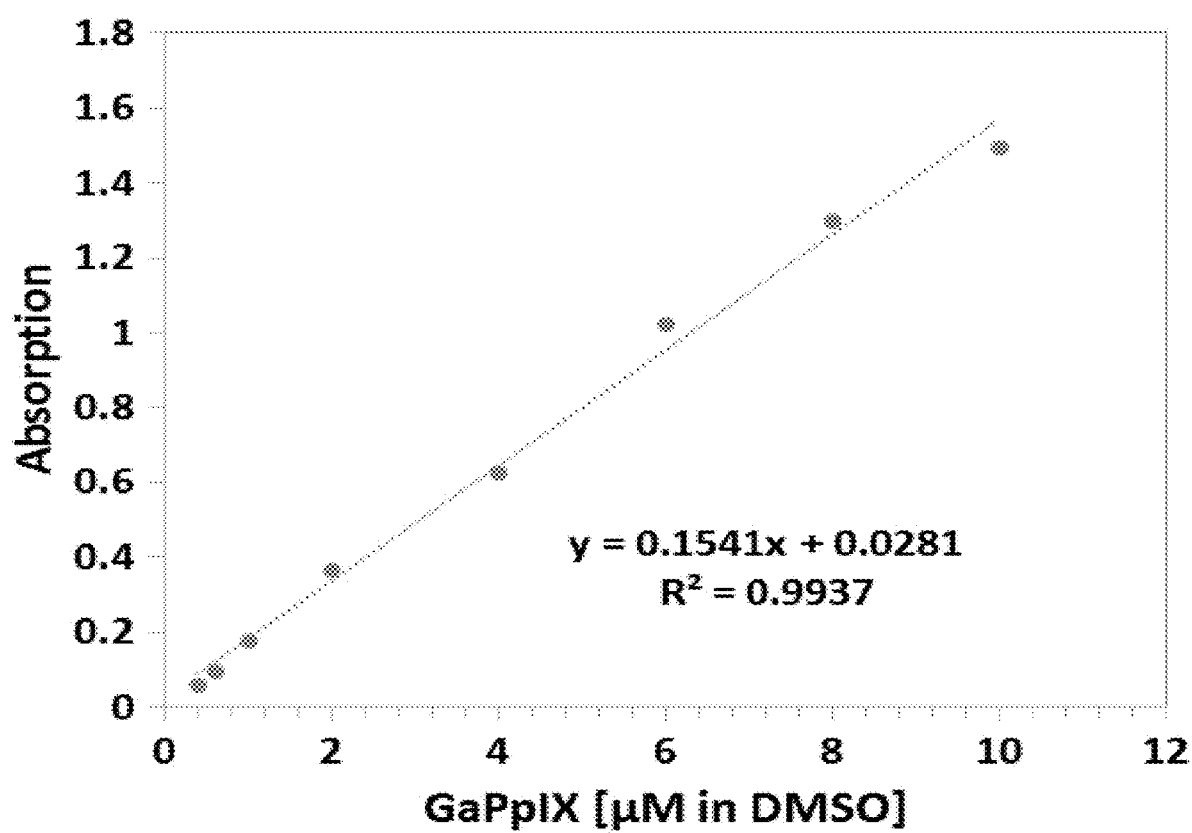
FIG. 7 depicts a Beer-Lambert plot of Ga-PpIX absorption in DMSO ($\lambda_{max}$=410 nm); best fit for $\varepsilon$=1.54×10$^5$ M$^{-1}$ cm$^{-1}$.

Absorption spectroscopy of Ga-PpIX 1 (0.4-10 µM in DMSO) yielded a mean molar extinction coefficient of $1.54 \times 10^5$ M$^{-1}$ cm$^{-1}$ (FIG. 7), lower than previous reports ($2.5 \times 10^5$ M$^{-1}$ cm$^{-1}$) (Rish, K. R.; Swartzlander, R.; Sadikot, T. N.; Berridge, M. V.; Smith, A. *Biochim. Biophys. Acta Bioenerg.* 2007, 1767, 1107-1117). The quantum yield of Ga-PpIX in deaerated DMSO was determined to be 6.3%, using Ru(II)(bipy)$_3$Cl$_2$ in aerated acetonitrile as a standard.

Microbiological Culture Under Iron-Deficient Conditions

For a complete list of all bacteria and culture media used in this study, see Table 2. Bacterial suspensions were first incubated for up to 16 hours in standard media at 37° C. in capped culture tubes, until an optical density of 1.0 was achieved (λ=600 nm). Bacteria were then subcultured during their rapid growth phase in media containing 3 mM 2,2'-bipyridine, with the exceptions of *B. anthracis* and *H. influenzae* which were subcultured in media containing 0.5 mM 2,2'-bipyridine, and *E. faecium* (VRE) which was subcultured in media supplemented with ethylenediaminetetraacetic acid (EDTA) or ethylenediamine di(o-hydroxyphenyl)acetic acid (EDDHA). We note that neither of these more stringent conditions were sufficient to induce the expression of hemin acquisition systems in VRE.

Bacterial Uptake of Hemin Analogs (Fluorescence Image Analysis)

Darkfield and fluorescent images were acquired in succession, with the former used to map regions of interest (ROIs) by tracing the outlines of bacteria (FIG. 8). Three images were acquired for each sample; in each case, the tracing map was overlaid onto the fluorescence image to calculate pixel intensities within each ROI, using the mean pixel intensity for quantitative analysis. Bacteria were also imaged without treatment with PpIX analogs, most of which produced values close to that of background except for *Salmonella enterica*, which served as the upper limit of autofluorescence (cf. FIG. 4). Data collection and image analyses were performed by the same user to ensure consistency for comparative analysis. We note that output values depend on multiple factors including fluorophore concentration, exposure times, choice of cutoff values and trace areas, and the inclusion of void spaces in ROIs which can reduce the mean values of reported intensities; nevertheless, variations between most replicate samples were observed to be within 10% (cf. Tables 4 and 5).

Fluorescence image analysis was also used to assess environmental factors on Ga-PpIX uptake. For example, the fur-dependent expression of high-affinity CSHRs in *S. aureus* was established by culturing strains in both standard and iron-limited conditions prior to treatment with Ga-PpIX at an early stage of logarithmic growth. Modest levels of fluorescence were observed for *S. aureus* raised in normal broth, but much higher levels could be observed for cultures grown under iron-limited conditions (FIG. 9). We note that growth in iron-deficient media induced a similarly strong response in *S. pneumoniae*, which did not acquire Ga-PpIX when cultured under normal conditions (data not shown).

Illumination Source for Antimicrobial Photodynamic Inactivation (aPDI)

Figure 10:
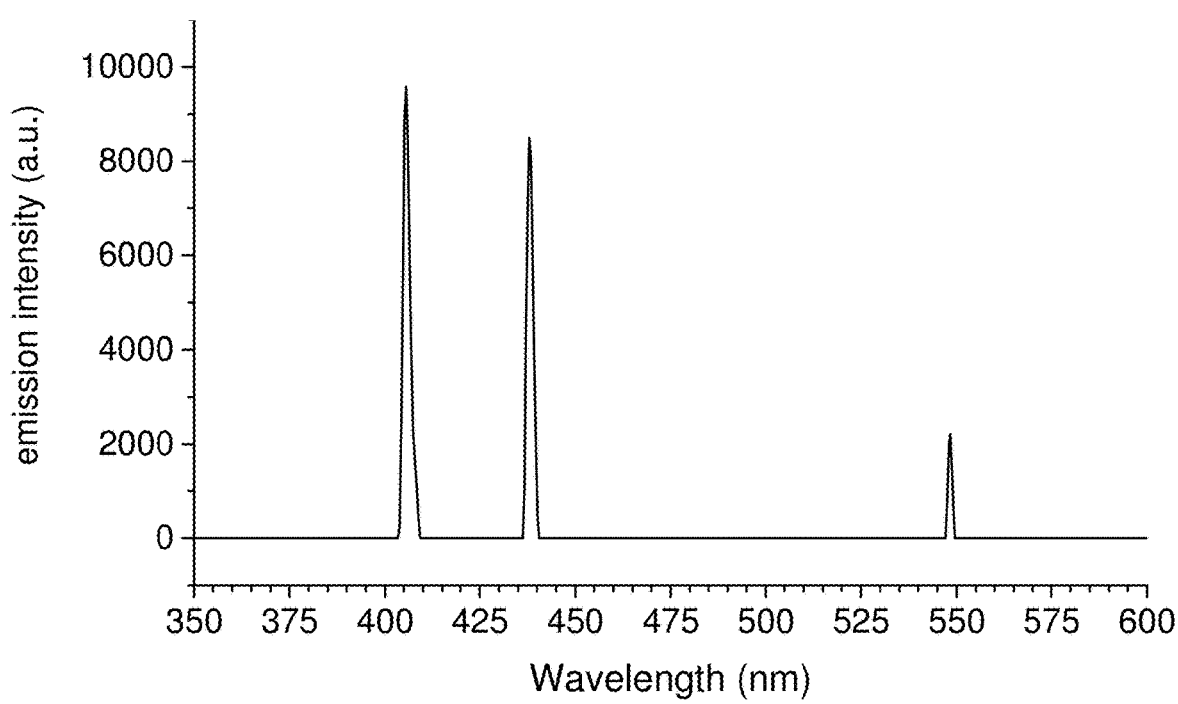
FIG. 10 depicts the emission spectrum for the CFL source, with a relative maximum at 406 nm (12.4 mW/cm$^2$) and also at 438 nm.

The irradiation source consisted of a 20-W compact fluorescent lightbulb (CFL; Sunlite SL20/BLB) housed in an ellipsoidal reflector dome. Emission spectra were measured with an Acton SpectraPro 2300i spectrometer (1200 gratings/inch), with major peaks at 406 and 438 nm and a minor peak at 548 nm (FIG. 10). Irradiance was measured with a handheld luminometer (Lux/FC HS1010A) positioned 4 cm from the CFL, yielding 91 lux or an average power density of 36.4 mW/cm$^2$; addition of a 425-nm or 408-nm shortpass filter yielded 31 lux or 12.4 mW/cm$^2$ corresponding with emission at 406 nm. The CFL produced only minor increases in temperature within the dome (28° C. after 15 min).

TABLE 3

Competitive uptake of PpIX derivatives by S. aureus (Fe-deficient conditions)[a]

| PpIX derivative | Fluorescence after 15 min (a.u.)[b] | Standard deviation | Fluorescence after 15 min exposure + 1 equiv. hemin (a.u.)[b] | Standard deviation |
|---|---|---|---|---|
| Ga-PpIX (1) | 42.55 | 0.95 | 10.0 | 1.10 |
| PpIX (2) | 16.70 | 0.50 | 9.4 | 0.57 |
| Zn-PpIX (3) | 31.45 | 2.66 | 16.87 | 0.45 |
| HP (4) | 14.38 | 1.82 | 9.58 | 0.47 |
| Zn-HP (5) | 29.2 | 4.8 | 14.52 | 0.06 |
| Ga-PpIX diMe (6) | 60.55 | 2.35 | 33.95 | 2.85 |
| PpIX diMe (7) | 15.75 | 0.75 | 12.75 | 0.18 |
| HP diMe (8) | 29.05 | 0.85 | 26.9 | 1 |
| DiAcHP diMe (9) | 21.6 | 0.2 | 18.95 | 0.65 |
| DiSuccHP diMe (10) | 19.37 | 0.33 | 16.9 | 1.6 |
| Ga-DiAcDP diMe (11) | 12.27 | 0.69 | 11.85 | 0.25 |
| DiAcDP diMe (12) | 20.9 | 0.35 | 18.05 | 0.85 |
| Verteporfin (13) | 30.75 | 0.95 | 28 | 1.4 |
| Background | 2.52 | 0.13 | — | — |
| Ctrl[−] (hemin only) | 2.55 | 0.26 | — | — |

[a]Cultured in TS media containing 3 mM bipy.
[b]Mean value of three independent measurements; no background subtraction was applied.

TABLE 4

Competitive uptake of PpIX derivatives by S. aureus (standard conditions)[a]

| PpIX derivative | Fluorescence after 15 min (a.u.)[b] | Standard deviation | Fluorescence after 15 min exposure + 1 equiv. hemin (a.u.)[b] | Standard deviation |
|---|---|---|---|---|
| Ga-PpIX (1) | 18.09 | 0.48 | 15.08 | 0.08 |
| PpIX (2) | 11.90 | 0.73 | 10.15 | 0.40 |
| Verteporfin (13) | 25.82 | 0.21 | 23.72 | 1.60 |

[a]Cultured in TS media.
[b]Mean value of three independent measurements; no background subtraction was applied.

TABLE 5

Time-dependent aPDI for staphylococci using 1 or 2 with CFL irradiation (406 nm)

| | GaPpIX (1) | | PpIX (2) | |
|---|---|---|---|---|
| Bacterial strain,[a] exposure time (fluence) | Antimicrobial activity, μM (3 log reduction) | Eradication, μM (6 log reduction) | Antimicrobial activity, μM (3 log reduction) | Eradication, μM (6 log reduction) |
| S. aureus (PCI 1203; ATCC 10537) | | | | |
| No irradiation (dark toxicity)[b] | >60 | 120 | 36 | 73 |
| 5 min (3.7 J/cm$^2$) | 3.75 | 15 | — | — |
| 15 min (11.2 J/cm$^2$) | 0.47 | 7.5 | 1.1 | 2.3 |
| MRSA USA200 (NRS 383) | | | | |
| No irradiation (dark toxicity)[b] | 36.3 | 73 | 36.3 | 146 |
| 15 min (11.2 J/cm$^2$) | 1.1 | 2.3 | 1.1 | 4.6 |
| MRSA USA500 (NRS 385) | | | | |
| No irradiation (dark toxicity)[b] | >146 | >146 | >146 | >146 |
| 15 min (11.2 J/cm$^2$) | 4.6 | 36.3 | 18.3 | 36.3 |
| MRSA USA700 (NRS 386) | | | | |
| No irradiation (dark toxicity)[b] | >146 | >146 | >146 | >146 |
| 15 min (11.2 J/cm$^2$) | 4.6 | 18.3 | 36.3 | 73 |

TABLE 5-continued

Time-dependent aPDI for staphylococci using 1 or 2 with CFL irradiation (406 nm)

| Bacterial strain,[a] exposure time (fluence) | GaPpIX (1) | | PpIX (2) | |
|---|---|---|---|---|
| | Antimicrobial activity, μM (3 log reduction) | Eradication, μM (6 log reduction) | Antimicrobial activity, μM (3 log reduction) | Eradication, μM (6 log reduction) |
| MRSA USA800 (NRS 387) | | | | |
| No irradiation (dark toxicity)[b] | 73 | 146 | >146 | >146 |
| 15 min (11.2 J/cm$^2$) | 1.1 | 2.3 | 9.1 | 18.3 |
| Staphylococcus epidermis (ATCC 155) | | | | |
| No irradiation (dark toxicity)[b] | 146 | 146 | >146 | >146 |
| 15 min (11.2 J/cm$^2$) | 0.57 | 4.5 | 4.5 | 9 |

[a]Cultured in Fe-deficient TS media (3 mM bipy).
[b]Bacteria incubated with Ga-PpIX for 15 min prior to plating.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than as specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A method for treating an infection caused by a bacteria comprising the steps of
a. applying a therapeutically effective amount of a metal-complexed porphyrin photosensitizer to an infected area, wherein said metal-complexed porphyrin has a formula (I)

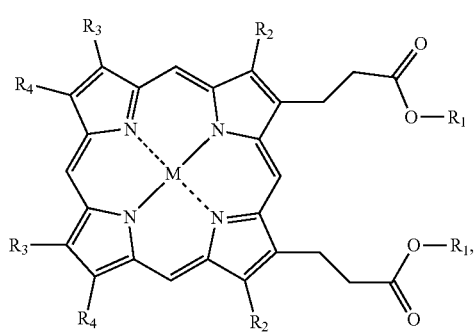

or a pharmaceutically acceptable salt thereof, wherein
M is a metal or coordinated metal ion;
R1 is hydrogen, an alkyl, or a substituted alkyl;
R2 is an alkyl, or a substituted alkyl;
R3 is an acyl, alkenyl, α-hydroxyalkyl, aryl, or aromatic heterocycle, each of which is optionally substituted; and
R4 is an alkyl, or a substituted alkyl;
wherein said bacteria express a high-affinity cell surface hemin receptor that specifically recognizes and binds to said metal-complexed porphyrin (I);
b. adding a nanoparticle to said photosensitizer; and then
c. exposing said infected area to a light for a period of time.

2. The method of claim 1, wherein said nanoparticle is a silver or gold nanoparticle.

3. The method of claim 1 further comprising a step of conjugating said photo sensitizer to an aminoglycoside antibiotic.

4. The method of claim 1, wherein $R_2$ and $R_4$ are methyl; $R_3$ is vinyl; and $R_1$ is methyl or hydrogen.

5. The method of claim 1, wherein M comprises a halo coordinated ion of magnesium, iron, manganese, cobalt, nickel, copper, zinc, and gallium.

6. The method of claim 5, wherein M is Ga(III)Cl.

7. The method of claim 1, wherein said light is a visible or infrared light.

8. The method of claim 7, wherein said light is a visible light of $\lambda_{max}$ about 405 nm.

9. The method of claim 1, wherein said infected area is a topical skin, a body or an inner body cavity that is accessible to light irradiation.

10. The method of claim 1, wherein said bacteria comprises Staphylococcus aureus, Methicillin-resistant Staphylococcus aureus (MRSA), vancomycin resistant S. aureus (VRSA), S. epidermidis, pathogenic staphylococci, Streptococcus mutans, S. pneumoniae, S. pyogenes, streptococci, corynebacteria, mycobacteria, and Bacillus anthracis.

* * * * *